United States Patent
Matsubara et al.

(10) Patent No.: US 10,238,816 B2
(45) Date of Patent: Mar. 26, 2019

(54) DEVICES AND METHODS FOR FORMING VASCULAR ACCESS

(71) Applicant: VOLCANO CORPORATION, San Diego, CA (US)

(72) Inventors: Bradley S. Matsubara, Escondido, CA (US); John Unser, Temecula, CA (US)

(73) Assignee: VOLCANO CORPORATION, San Diego, CA (US)

( * ) Notice: Subject to any disclaimer, the term of this patent is extended or adjusted under 35 U.S.C. 154(b) by 514 days.

(21) Appl. No.: 14/596,699

(22) Filed: Jan. 14, 2015

(65) Prior Publication Data

US 2015/0209526 A1 Jul. 30, 2015

Related U.S. Application Data

(60) Provisional application No. 61/927,054, filed on Jan. 14, 2014.

(51) Int. Cl.
*A61B 1/00* (2006.01)
*A61M 5/42* (2006.01)
(Continued)

(52) U.S. Cl.
CPC ......... *A61M 5/427* (2013.01); *A61B 1/00009* (2013.01); *A61B 1/05* (2013.01);
(Continued)

(58) Field of Classification Search
CPC ...... A61M 5/427; A61B 1/05; A61B 1/00009; A61B 17/11; A61B 17/3478; A61B 2017/1107; A61B 2017/22044; A61B 2090/3735; A61B 2017/1425
See application file for complete search history.

(56) References Cited

U.S. PATENT DOCUMENTS

| 4,794,931 A | 1/1989 | Yock |
| 4,841,977 A | 6/1989 | Griffith et al. |

(Continued)

FOREIGN PATENT DOCUMENTS

| CA | 2 616 760 A1 | 2/2007 |
| EP | 1 820 436 A2 | 8/2007 |

(Continued)

OTHER PUBLICATIONS

Anonymous, 2006, Clinical Practice Guidelines and Clinical Practice Recommendations 2006 Updates, National Kidney Foundation:10PP.

(Continued)

*Primary Examiner* — Timothy J Neal

(57) ABSTRACT

The invention generally relates to catheter systems and methods for guided formation of vascular access sites (such as fistulas and grafts). According to certain aspects, a catheter system for forming a vascular access site include an elongate body comprising a distal end and configured to be inserted into a first vessel. The elongate body includes an exit port along its side that is proximal to the distal end. An imaging assembly is associated with the elongate body and configured to generate image data of the first vessel and a second vessel positioned next to the first vessel. For vascular access formation, a penetrating member of the catheter system extends out of the exit port and through a wall of the first vessel and a wall of the second vessel.

9 Claims, 10 Drawing Sheets

(51) Int. Cl.
*A61B 17/34* (2006.01)
*A61B 1/05* (2006.01)
*A61B 18/14* (2006.01)
*A61B 17/00* (2006.01)
*A61B 17/11* (2006.01)
*A61B 17/22* (2006.01)
*A61B 90/00* (2016.01)

(52) U.S. Cl.
CPC .......... *A61B 17/11* (2013.01); *A61B 17/3478* (2013.01); *A61B 18/1492* (2013.01); *A61B 2017/00252* (2013.01); *A61B 2017/1107* (2013.01); *A61B 2017/1139* (2013.01); *A61B 2017/22044* (2013.01); *A61B 2018/1425* (2013.01); *A61B 2090/3735* (2016.02); *A61B 2090/3784* (2016.02)

(56) References Cited

U.S. PATENT DOCUMENTS

| | | |
|---|---|---|
| 4,917,097 A | 4/1990 | Proudian et al. |
| 4,951,677 A | 8/1990 | Crowley et al. |
| 5,000,185 A | 3/1991 | Yock |
| 5,095,911 A | 3/1992 | Pomeranz |
| 5,125,137 A | 6/1992 | Corl et al. |
| 5,135,486 A | 8/1992 | Eberle et al. |
| 5,163,445 A | 11/1992 | Christian et al. |
| 5,167,233 A | 12/1992 | Eberle et al. |
| 5,174,295 A | 12/1992 | Christian et al. |
| 5,176,141 A | 1/1993 | Bom et al. |
| 5,178,159 A | 1/1993 | Christian |
| 5,183,048 A | 2/1993 | Eberle |
| 5,226,421 A | 7/1993 | Frisbie et al. |
| 5,240,003 A | 8/1993 | Lancee et al. |
| 5,240,437 A | 8/1993 | Christian |
| 5,243,988 A | 9/1993 | Sieben et al. |
| 5,313,949 A | 5/1994 | Yock |
| 5,321,501 A | 6/1994 | Swanson et al. |
| 5,326,342 A | 7/1994 | Pflueger et al. |
| 5,348,017 A | 9/1994 | Thornton et al. |
| 5,353,798 A | 10/1994 | Sieben |
| 5,368,037 A | 11/1994 | Eberle et al. |
| 5,372,138 A | 12/1994 | Crowley et al. |
| 5,373,845 A | 12/1994 | Gardineer et al. |
| 5,373,849 A | 12/1994 | Maroney et al. |
| 5,375,602 A | 12/1994 | Lancee et al. |
| 5,453,575 A | 9/1995 | O'Donnell et al. |
| 5,771,895 A | 6/1998 | Slager |
| 5,830,222 A * | 11/1998 | Makower ............ A61B 1/3137 604/99.03 |
| 5,873,835 A | 2/1999 | Hastings et al. |
| 6,068,638 A | 5/2000 | Makower |
| 6,106,476 A | 8/2000 | Corl et al. |
| 6,134,003 A | 10/2000 | Tearney et al. |
| 6,159,225 A | 12/2000 | Makower |
| 6,190,353 B1 | 2/2001 | Makower et al. |
| 6,200,268 B1 | 3/2001 | Vince et al. |
| 6,210,339 B1 | 4/2001 | Kiepen et al. |
| 6,283,951 B1 | 9/2001 | Flaherty et al. |
| 6,375,615 B1 * | 4/2002 | Flaherty ............... A61F 2/2493 600/439 |
| 6,381,350 B1 | 4/2002 | Klingensmith et al. |
| 6,421,164 B2 | 7/2002 | Tearney et al. |
| 6,457,365 B1 | 10/2002 | Stephens et al. |
| 6,508,824 B1 | 1/2003 | Flaherty et al. |
| 6,544,230 B1 | 4/2003 | Flaherty et al. |
| 6,551,250 B2 | 4/2003 | Khalil |
| 6,579,311 B1 | 6/2003 | Makower |
| 6,602,241 B2 | 8/2003 | Makower et al. |
| 6,655,386 B1 | 12/2003 | Makower et al. |
| 6,659,957 B1 | 12/2003 | Vardi et al. |
| 6,660,024 B1 | 12/2003 | Flaherty et al. |
| 6,669,709 B1 | 12/2003 | Cohn et al. |
| 6,685,648 B2 | 2/2004 | Flaherty et al. |
| 6,709,444 B1 | 3/2004 | Makower |
| 6,726,677 B1 | 4/2004 | Flaherty et al. |
| 6,746,464 B1 | 6/2004 | Makower |
| 6,780,157 B2 | 8/2004 | Stephens et al. |
| 7,074,188 B2 | 7/2006 | Nair et al. |
| 7,175,597 B2 | 2/2007 | Vince et al. |
| 7,215,802 B2 | 5/2007 | Klingensmith et al. |
| 7,245,789 B2 | 7/2007 | Bates et al. |
| 7,359,554 B2 | 4/2008 | Klingensmith et al. |
| 7,387,636 B2 | 6/2008 | Cohn et al. |
| 7,447,388 B2 | 11/2008 | Bates et al. |
| 7,463,759 B2 | 12/2008 | Klingensmith et al. |
| 7,527,594 B2 | 5/2009 | Vardi et al. |
| 7,660,492 B2 | 2/2010 | Bates et al. |
| 7,736,317 B2 | 6/2010 | Stephens et al. |
| 7,783,337 B2 | 8/2010 | Feldman et al. |
| 7,787,127 B2 | 8/2010 | Galle et al. |
| 7,995,210 B2 | 8/2011 | Tearney et al. |
| 7,999,938 B2 | 8/2011 | Wang |
| 8,059,923 B2 | 11/2011 | Bates et al. |
| 8,108,030 B2 | 1/2012 | Castella et al. |
| 8,486,062 B2 | 7/2013 | Belhe et al. |
| 8,486,063 B2 | 7/2013 | Werneth et al. |
| 2002/0010487 A1 | 1/2002 | Evans et al. |
| 2004/0146546 A1 | 7/2004 | Gravett et al. |
| 2005/0196026 A1* | 9/2005 | Klingensmith .... A61B 5/02007 382/128 |
| 2005/0249391 A1 | 11/2005 | Kimmel et al. |
| 2006/0111704 A1* | 5/2006 | Brenneman ............ A61B 17/11 606/41 |
| 2006/0241342 A1 | 10/2006 | Macaulay et al. |
| 2007/0016034 A1 | 1/2007 | Donaldson |
| 2007/0232933 A1 | 10/2007 | Gille et al. |
| 2008/0119739 A1 | 5/2008 | Vardi et al. |
| 2008/0171944 A1 | 7/2008 | Brenneman et al. |
| 2008/0180683 A1 | 7/2008 | Kemp |
| 2008/0291463 A1 | 11/2008 | Milner et al. |
| 2009/0018393 A1 | 1/2009 | Dick et al. |
| 2009/0024085 A1 | 1/2009 | To et al. |
| 2009/0043191 A1 | 2/2009 | Castella et al. |
| 2009/0088650 A1 | 4/2009 | Corl |
| 2009/0195514 A1 | 8/2009 | Glynn et al. |
| 2009/0284332 A1 | 11/2009 | Moore et al. |
| 2010/0087732 A1 | 4/2010 | Eberle et al. |
| 2010/0130864 A1 | 5/2010 | Donnelly et al. |
| 2010/0220334 A1 | 9/2010 | Condit et al. |
| 2011/0060229 A1 | 3/2011 | Hulvershorn et al. |
| 2011/0152771 A1 | 6/2011 | Milner et al. |
| 2011/0306995 A1 | 12/2011 | Moberg |
| 2011/0319752 A1 | 12/2011 | Steinberg et al. |
| 2012/0108943 A1 | 5/2012 | Bates et al. |
| 2012/0230565 A1 | 9/2012 | Steinberg et al. |
| 2013/0030295 A1 | 1/2013 | Huennekens et al. |
| 2013/0030303 A1 | 1/2013 | Ahmed et al. |
| 2013/0046167 A1 | 2/2013 | Shah |
| 2013/0137980 A1 | 5/2013 | Waters et al. |
| 2013/0150716 A1 | 6/2013 | Stigall et al. |
| 2013/0296704 A1 | 11/2013 | Magnin et al. |
| 2013/0303907 A1 | 11/2013 | Corl |

FOREIGN PATENT DOCUMENTS

| | | |
|---|---|---|
| JP | 5237111 A | 9/1993 |
| JP | 5285140 A | 11/1993 |
| JP | 2007089901 A | 4/2007 |
| WO | 91/17710 A1 | 11/1991 |
| WO | 03/030744 A1 | 4/2003 |
| WO | 2014/100226 A1 | 6/2014 |
| WO | 2014/109879 A1 | 7/2014 |
| WO | 2014/143816 A1 | 9/2014 |
| WO | 2014/150401 A1 | 9/2014 |

OTHER PUBLICATIONS

Bail et al.; 'Optical coherence tomography with the "Spectral Radar"—Fast optical analysis in volume scatterers by short coherence interferometry' Optics letters vol. 21, No. 14 (1996) 1087-1089.

(56) References Cited

OTHER PUBLICATIONS

Ferring, et al., Vascular ultrasound for the pre-operative evaluation prior to arteriovenous fistula formation for haemodialysis: review of the evidence, Nephrol. Dial. Transplant. 23(6):1809-1815, 2008.
Fleming et al., "Real-time monitoring of cardiac radio-frequency ablation lesion formation using an optical coherence tomography forward-imaging catheter. ," J. Biomed. Opt. 15, (3 ), 030516-030513 (2010).
Harrison et al., What's in a name?, J Endo Ther 14(6):797-801, 2011.
International Search Report and Written Opinion dated Apr. 10, 2015, for International Patent Application No. PCT/US2015/011397, filed Jan. 14, 2015 (14 pages).
International Search Report and Written Opinion dated Apr. 21, 2015, for International Patent Application No. PCT/US2015/011359, filed Jan. 14, 2015 (10 pages).
International Search Report and Written Opinion dated Apr. 28, 2015, for International Patent Application No. PCT/US2015/011357, filed Jan. 14, 2015 (11 pages).
International Search Report and Written Opinion dated Apr. 28, 2015, for International Patent Application No. PCT/US2015/011411, filed Jan. 14, 2015 (11 pages).
International Search Report and Written Opinion dated May 4, 2015, for International Patent Application No. PCT/US2015/011337, filed Jan. 14, 2015 (16 pages).
Kirkman, 1991, Technique for flow reduction in dialysis access fistulas, Surg Gyn.
Mickley, 2008, Steal Syndrome-strategies to preserve vascular access and extremity, Nephrol Dial Transplant 23:19-24.
Miller et al., 2006, Minimally Invasive Limited Ligation Endoluminal-assisted Revision (MILLER) for treatment of dialysis access-associated steal syndrome, Kidney Int 70(4):765-70.
Miller, et al., 2009, The MILLER banding procedure is an effective method for treating dialysis-associated steal syndrome, Kidney Int 1-8.
Rivers, et al., 1992, Correction of steal syndrome secondary to hemodialysis access fistulas: a simplified quantitative technique, Surgery 112(3):593-7.
Robbin, et al., Hemodialysis arteriovenous fistula maturity: US evaluation, Radiology 225(1):59-64, 2002.
Schneider, et al., 2006, T-banding: A technique for flow reduction of a hyper-functioning arteriovenous fistula, J Vasc Surg.
Seward et al., Mayo Clinic Proceedings 71(7):629-635 (1996).
Smith et al., 'Absolute displacement measurements using modulation of the spectrum of white light in a Michelson interferometer' Applied Optics, vol. 28, No. 15, 1989, 3339-3342.
Toregeani et al., Evaluation of hemodialysis arteriovenous fistula maturation by color-flow Doppler ultrasound, J Vasc Bras 7(3):203-2013, 2008.
Wang et al. "In vivo intracardiac optical coherence tomography imaging through percutaneous access: toward image-guided radio-frequency ablation". J. Biomed. Opt. 0001;16(11):110505-110505-3. doi:10.1117/1.3656966.
Wang et al., "Optimizing the Beam Pattern of a Forward-Viewing Ring-Annular Ultrasound Array for Intravascular Imaging", Transactions on Ultrasonics, Ferroelectrics, and Frequency Control, vol. 49, No. 12, Dec. 2002.
West et al., Arterial insufficiency in hemodialysis access procedures: correction by banding technique, Transpl Proc 23(2): 1838-40, 1991.

\* cited by examiner

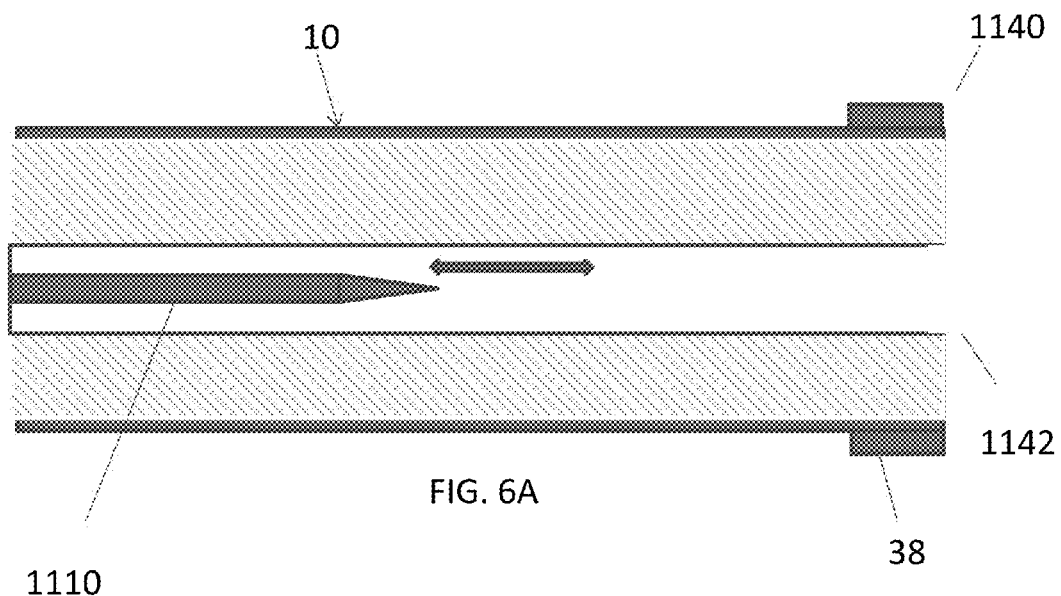
FIG. 6A
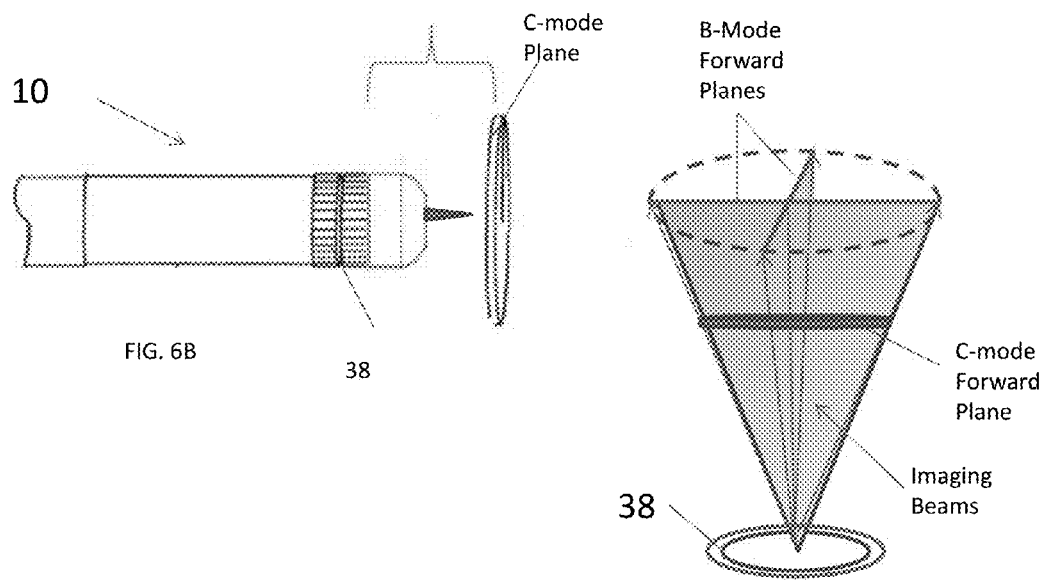
FIG. 6B
FIG. 6C

DEVICES AND METHODS FOR FORMING VASCULAR ACCESS

CROSS-REFERENCE TO RELATED APPLICATIONS

This application claims the benefit of, and priority to, U.S. Provisional Application Ser. No. 61/927,054, filed Jan. 14, 2014, the content of which is incorporated by reference herein in its entirety.

TECHNICAL FIELD

The present invention relates to devices and methods for guided vascular access creation.

BACKGROUND

Healthy kidneys remove waste and minerals from the blood. When kidneys fail, harmful waste builds up in the body, blood pressure may rise, and the body may retain excess fluid and not make enough red blood cells due to, for example, insufficient erythropoietin production. Hemodialysis is a common method for treating kidney failures and involves flowing blood through a filter to remove waste. Before hemodialysis can be done, a vascular access site must be formed that connects an artery to a vein and provides a way for dialysis tubes to access the artery and vein. The vascular access allows blood from the artery to travel through tubes into a filter of a dialysis machine that purifies the blood and then returns the purified blood back into the vein.

Currently, there are two main forms of permanent hemodialysis vascular access: native arteriovenous (AV) fistulas and synthetic AV grafts. An AV fistula is an induced native channel formed to connect an artery to a vein, whereas AV graft is an artificial channel that connects the artery to the vein. Both forms of vascular access sites often require a surgical procedure to generate openings in the vein and artery that eventually form the natural channel (i.e. anastomosis). After the openings are created, sutures or a clip are used to ligate the vein to the artery while the fistula matures. In contrast to AV fistulas, an AV graft is typically a synthetic looped tube that is surgically inserted to connect the opening of the artery with the opening of the vein.

Surgical vascular access creation typically involves inserting a catheter into the vein or artery to form openings between the vessels and requires precise execution for several reasons. First, a surgeon must approximate a location where the vein is in close proximity to the artery so that a connection can form between the two. In addition, current procedures also require a needle to deploy through the walls of both the vein and the artery. These factors combined can result one or more openings being created in either vessel that are unsuitable for fistula creation. For example, one may inadvertently create a hole in a vein at a location where the artery is too far away to form the vascular access site via anastomosis. In another example, if the needle is not properly positioned to deploy where the vein wall is positioned next to the arterial wall, one risks forming an wall opening in the vein at a location that cannot be aligned with the wall of the artery (e.g. opening of vein opposes wall of artery).

SUMMARY

The present invention utilizes intravascular imaging to guide and facilitate vascular access creation (e.g., formation of fistulas and grafts) for hemodialysis. The intravascular images provide for visualization of both vessels subject to vascular access formation and evaluation of tissue and blood flow characteristics during the procedure. With the enhanced guidance provided by the present catheter systems, the risk of unnecessarily injuring the vessel and the potential for creating an opening unsuitable for forming vascular access is substantially decreased. In some embodiments, spectral analysis tools are used in conjunction with imaging to further improve visualization of factors that contribute to a vessel's health (such as any sclerosis, atheroma deposits, and/or thrombus morphology (i.e., virtual histology)), and thus its suitability for vascular access formation.

Catheter systems of the invention are configured to form a vascular access site between a first vessel and a second vessel. Typically, the vascular access site is created between an artery and a vein to form a fistula in order to support hemodialysis. In certain aspects, a catheter system of the invention includes an elongate body and is insertable into a vessel of the vasculature. The elongate body includes a distal end and an exit port located on its side that is proximal to the distal end. The catheter system further includes an imaging assembly associated with the elongate body. The imaging assembly is configured to generate imaging data of a first vessel (i.e. a vessel in which the catheter system is introduced) and a second vessel positioned next to the first vessel. In order to form the vascular access site, a point member is deployable out of the side exit port such that the penetrating member extends through walls of the first and second vessels.

The imaging assembly of the catheter systems advantageously allows one to determine an ideal location for forming a fistula because both vessels needed for vascular access can be imaged simultaneously. The imaging assembly may be a forward-viewing imaging element, a side-viewing imaging element, or a combination thereof. Suitable imaging assemblies include ultrasound imaging assemblies and optical coherence tomography imaging assemblies.

In addition to imaging both vessels, the obtained image data can be subject to data processing (e.g., spectral analysis) such that tissue and blood of both vessels can be characterized. Processing techniques for characterizing objects present in the image data may include, for example, determining the density of the biological material of one or more vessels, determining the composition of the biological material of one or more vessels, determining a blood-tissue border of the lumen of the one or more vessels. Using the information obtained from processing, one can determine a location where the vessels are positioned next to each other and where the health of both vessels is ideal to support fistula formation.

Catheter systems of the invention include a penetrating member that is deployed from the elongate body in order to form an opening at least two vessels for vascular access creation. In certain embodiments, the penetrating member is a penetrating guidewire. In other embodiments, the penetrating member is a needle. The needle or guidewire may include one or more ablation elements configured to cauterize vessel tissue that defines the created openings and eventually forms the fistula or site for the AV graft. Alternatively, the needle may define a lumen and a cauterizing element may extend from the lumen to cauterize the vascular access vessel tissue. The cauterization of the vascular access tissue advantageously inhibits formation of intimal hyperplasia, which can prevent the vascular access site from maturing into a fistula.

After formation of one or more openings, an anastomotic device (such as a clip) can be delivered into the openings to facilitate maturation of the vascular access site. In certain embodiments, the anastomotic device is guided over the penetrating guidewire (being disposed within the opening) and deployed into the opening. The penetrating guidewire can be retracted leaving the anastomotic device secured between the two openings of the vessels.

BRIEF DESCRIPTION OF THE DRAWINGS

FIGS. 6A-6B illustrates forward-looking catheter systems of the invention according to certain embodiments.

FIG. 6C illustrates beamformer geometry of a forward looking catheter system according to some embodiments.

DETAILED DESCRIPTION

Catheter systems and methods of the invention utilize intravascular imaging to guide and facilitate vascular access creation (e.g., either fistulas or grafts) for hemodialysis. An arteriovenous (AV) fistula is an induced native channel formed to connect an artery to a vein, whereas AV graft is an artificial connection (such as a synthetic material) that connects the artery to the vein. In addition, the term "fistula" is commonly used to generally describe both native and artificial connections between arteries and veins. The intravascular images provide provides for visualization of both vessels subject to vascular access formation and evaluation of tissue and blood flow characteristics during the procedure. With the enhanced guidance provided by catheter systems, the risk of unnecessarily injuring the vessel and the potential for creating an opening unsuitable for forming vascular access is substantially decreased. In some embodiments, spectral analysis tools are used in conjunction with imaging to further improve visualization of factors that contribute to a vessel's health (such as any sclerosis, atheroma deposits, and/or thrombus morphology (i.e., virtual histology)), and thus its suitability for vascular access formation.

As discussed briefly in the background, hemodialysis is commonly used to "clean" the blood of a patient having compromised kidney function, due, e.g., to disease or injury. Hemodialysis is typically accomplished with a dialysis machine that essentially serves as an artificial kidney by removing the by-products of metabolism, as well as excess water, from the blood. The machine typically includes a filter, constructed from semipermeable membranes, and a pump. The semipermeable membranes are arranged in multiple pleated sheets or small caliber tubes to increase the surface area across which dialysis takes place. The pump pulls blood from the patient through one line (afferent line) and returns the blood through a second line (efferent line). The same pump also pressurizes the blood to overcome the resistance caused by the membrane.

Figure 1:
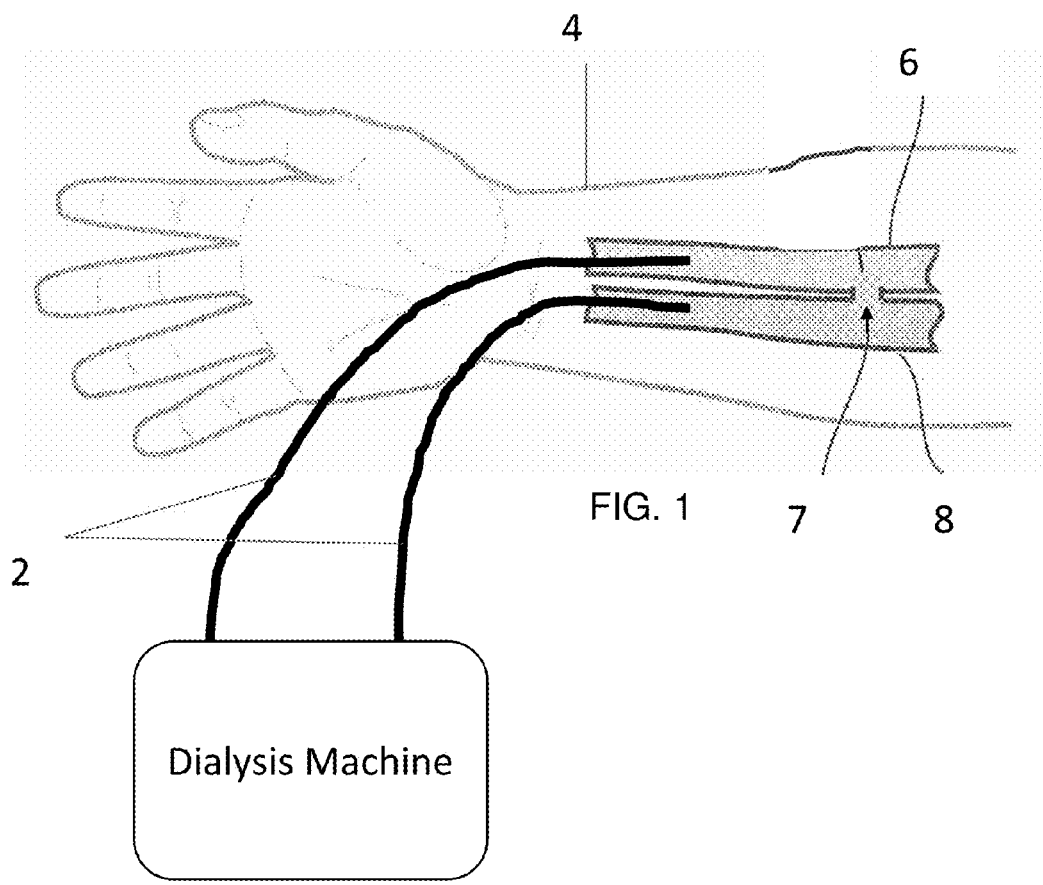
FIG. 1 depicts an arteriovenous fistula from the brachial artery to the brachial vein used to speed hemodialysis in a patient with compromised renal function.

For multiple reasons, the process is time sensitive. First, blood must be returned to the patient as rapidly as it is withdrawn to avoid complications from large fluctuations in intravascular volume, i.e., organ damage or shock. Secondly, dialysis patients typically need to undergo treatment two to four times per week, thus a lengthy dialysis procedure severely limits the patients productive hours. Accordingly, the afferent and efferent connections are typically coupled to large bore, high flow blood vessels 6, 8 (located in a limb 4) by way of transcutaneous catheters 2, such as shown in FIG. 1. To perform hemodialysis, two large bore needles are sterilely introduced into the graft lumen through the intact skin. This can be readily accomplished as the graft, in its subcutaneous location, is easily palpated. The large lumen and high blood flow provide excellent drainage for dialysis. After hemodialysis is completed, the needles are removed, so no permanent breech in the skin exists. Each time the patient is dialyzed, needles are reintroduced.

In order to speed the dialysis process, the peripheral vessels of the limb are typically bypassed by creating a fistula 7 between larger vessels 6, 8 in the limb 4, e.g., as shown in FIG. 1. This surgically created "short circuit" in the circulatory system is referred to as a shunt. The low resistance in the shunt allows higher blood flows through the dialysis machine. In some instances, the fistula is merely a connection between a closely-spaced artery 6 and vein 8, e.g., between the brachial artery and the antecubital veins, as shown in FIG. 1. Fistula creation can be accomplished by creating an incision in the limb 4, dissecting the vessels, creating a small opening in both vessels and then suturing or clipping the openings together. Eventually, as the vein 8 and artery 6 heal, the fistula 7 matures to form a natural channel between the two.

While methods and devices of the invention are described with regard to forming vascular access sites for hemodialysis, the invention can be utilized to create other vascular access sites and access sites for other systems. For example, to create access sites in the respiratory system, digestive system, and circulatory system.

Catheter systems of the invention incorporate one or more imaging assemblies to provide for guide and informed fistula formation in a manner not possible in prior art fistula creation procedures. FIGS. 2A-6C generally illustrate catheter systems for guided fistula formation in accordance with various aspects and embodiments of the invention.

Figure 2A:
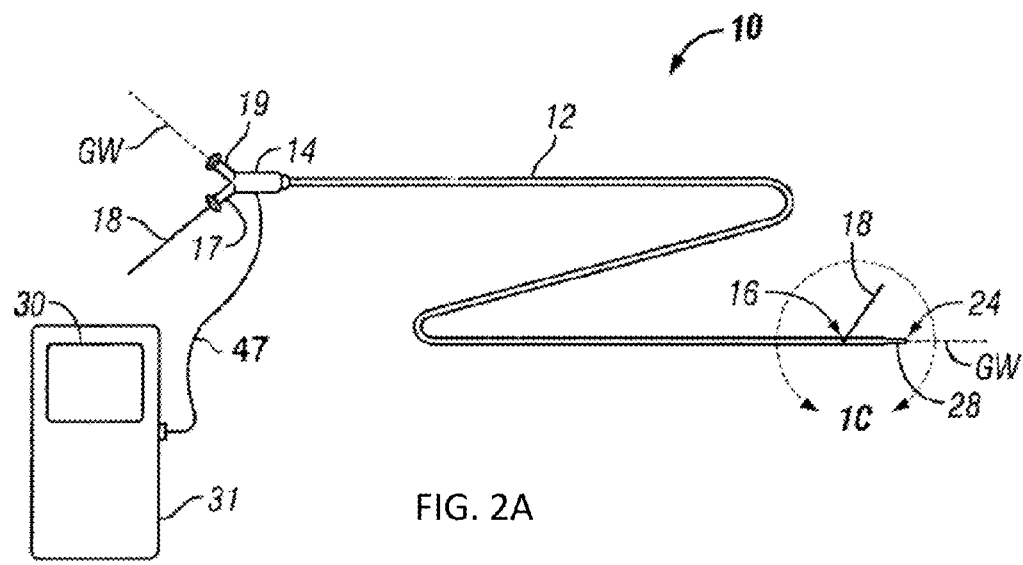
FIG. 2A illustrates a catheter system for forming vascular access sites according to certain embodiments.
Figure 3A:
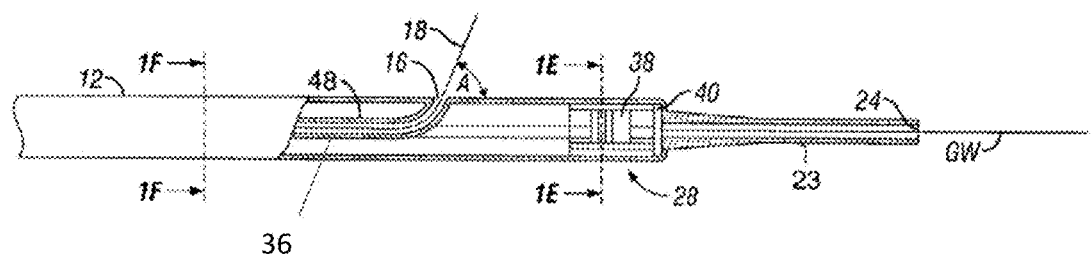
FIG. 3A depicts a distal portion of the catheter system shown in FIG. 2A.
Figure 3B:
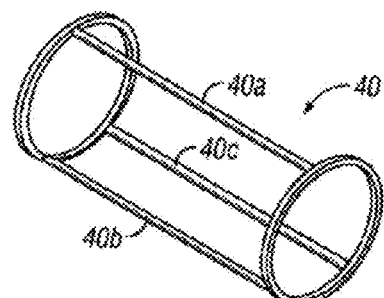
FIG. 3B is an enlarged view of a marker structure of the catheter system of FIG. 2A.
Figure 3C:
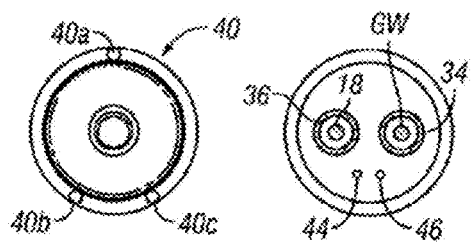
FIG. 3C is a cross-sectional view through line 1E-1E of FIG. 2A.
Figure 3D:
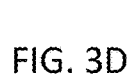
FIG. 3D is a cross-sectional view through line 1F-1F of FIG. 2A.

FIG. 2A generally shows one embodiment of a fistula forming catheter system 10 of the present invention. This system 10 comprises a flexible elongate body 12 having a proximal hub 14 with female Luer ports 17, 19, a side exit port 16 and a distal end 24 defining an opening. The side exit port 16 being proximal to the distal end 24 of the flexible elongate body 12. In addition and as shown in FIG. 3A, the elongate body 12 may include an optional tapered distal tip section 23 formed of material that is softer and more flexible than the adjacent distal portion of the elongate body 12.

In order to form an opening for a fistula, a needle or a penetrating guidewire can be extended out of the side exit port 16 and into one or more vessel walls substantially parallel to and next to the side exit port 16. The needle or penetrating guidewire are extendable and retractable. In FIG. 2A, a penetrating guidewire 18 is shown that can be used to form the vessel wall openings for vascular access creation. Exemplary penetrating guidewires 18 include 0.014 in. diameter trocar or stiff guidewire available as (e.g. PERSUADER® 9 guidewire, from Medtronic Vascular, Inc., Santa Rosa, Calif. or ASAHI CONFIANZA®, Abbott Vascular, Redwood City, Calif.). In other embodiments, the penetrating guidewire is a modified flow or pressure guidewire sold under the name FLOWIRE by Volcano Corporation, the pressure guidewire sold under the name PRIMEWIRE PRESTIGE by Volcano Corporation, or both. Those guidewires can be modified to incorporate a tissue penetrating tip.

As an alternative to the penetrating guidewire 18, a needle can be used to create the vessel openings for vascular access. For embodiments that utilize a needle, the needle may define an opening through which a guidewire can be driven through after the needle forms the vascular access openings. The penetrating guidewire 18 or needle is insertable through port 17 on the proximal hub 14 and is advanceable through the elongate body 12 and out of side outlet opening 16. The needle and penetrating guidewire 18 are discussed in more detail with reference to FIGS. 2C-2E.

Optionally, a tracking guidewire (over-the-wire guidewire) is insertable into port 19 on proximal hub 14 and can be advanced through the elongate body 12 and out of distal end opening 24. The catheter system 10 can be ridden over the tracking guidewire to reach the location of interest within the vasculature for fistula formation. A suitable tracking guidewire includes a 0.014 in. diameter guidewire, such as the COUGAR® guidewire from Medtronic Vascular, Inc., Santa Rosa, Calif. As an alternative to the "over-the-wire" design shown in the drawings, a "rapid exchange" version of the catheter system 10 may also be used. In such rapid exchange version of the catheter, the port 19 on proximal hub 14 would be replaced by a tracking guidewire insertion port located on the side of the elongate body 12 a spaced distance (e.g., 15-30 cm) from its distal end.

Figure 2B:
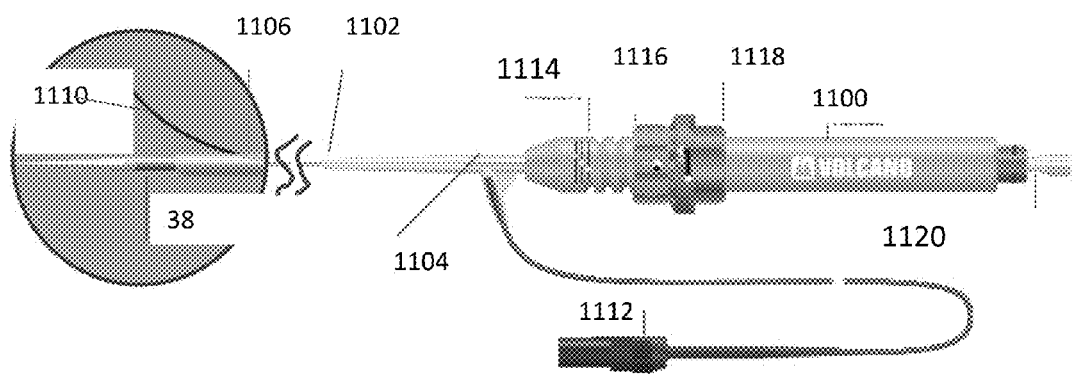
FIG. 2B illustrates another catheter system for forming vascular access sites according to other embodiments.

FIG. 2B illustrates an alternative embodiment of a catheter system 10 of the invention. As shown in FIG. 2B, the catheter system 10 includes a handle 1100 associated with a Y-junction 1104 that is coupled to the elongate catheter body 1102. At a distal portion of the elongate body 1102, the catheter includes an imaging assembly 1108 (such as IVUS phased array transducer) for imaging and an exit port 1106 located on the side of the distal portion. A needle 1110 is shown in the extended position, i.e. deployed out of the exit port 1106. The needle 1110, as described in more detail below, may include a lumen through which a guidewire or cauterizing element may be deployed. The exit port 1106 is located just proximal to the imaging assembly 1108. This positioning allows one to utilize the imaging assembly 1108 to image a target location for needle deployment and to image the needle 1110 as it is deployed into one or more vessel walls to form the openings required for vascular access creation. At the Y junction 1107, the electrical wires and other connections required for the imaging assembly 1110 are coupled to a connector 1112. The connector 1112 plugs into an imaging console (e.g. console 31) that allows an operator to obtain and display real-time images of the procedure. Suitable consoles include Volcano Corporation's s5i or s5 Imaging Systems. The handle 1100 may include a needle depth marker 1114 that allow one to determine how far the needle has deployed from the needle exit port 1106. The handle 1100 may also include a needle stop ring 1116 with an optional lock that prevents the needle from being deployed a certain extent, and can be used to maintain the positioning of the needle 1110. In addition, the handle may include a needle deployment mechanism 1118 that allows for easy deployment and retraction of the needle 1110. The needle deployment mechanism 1118 may be a sliding mechanism that deploys/retracts the needle by sliding the mechanism forward and backwards or may be a turning mechanism that deploys/retracts the needle by rotation. The needle 1110 can be loaded into the catheter 10 through the proximal end 1120. Optionally, a guidewire for insertion into the needle 1110 and/or a tracking guidewire may also be inserted into the catheter system 10 through the proximal end 1120.

As may be appreciated from FIGS. 2A and 3A, for example, the catheter 12 has a tracking guidewire lumen 34 and a penetrating guidewire lumen 36. A curved, substantially rigid tubular member 48 may be located at the distal end of the penetrating guidewire lumen 36 and serves as a guide surface which deflects the penetrating guidewire 18 or needle 1110 out of the side exit port 16, 1106.

The catheters systems of invention, such as those in FIGS. 2A, 2B, 3A, 5, 6A-6C, may be described as either including a penetrating guidewire or a penetrating needle for vascular access creation. It is understood that any of the embodiments of the catheter system herein can be adapted to include either a penetrating guidewire or penetrating needle.

Figure 2C:
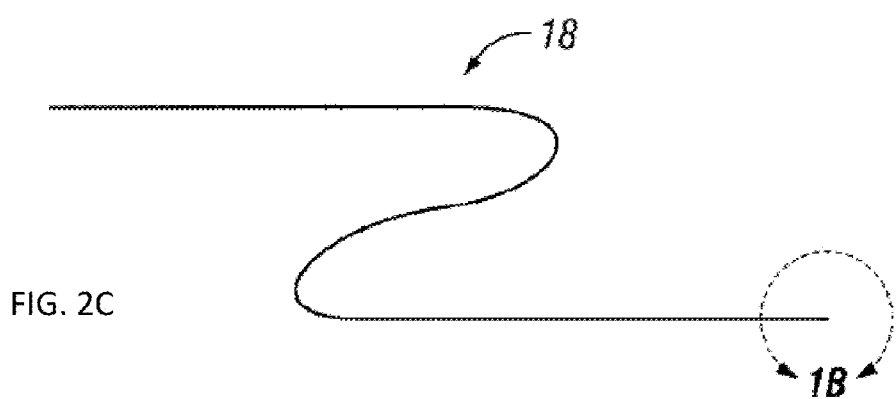
FIG. 2C illustrates a penetrating guidewire of the catheter system according to certain embodiments.
Figure 2D:
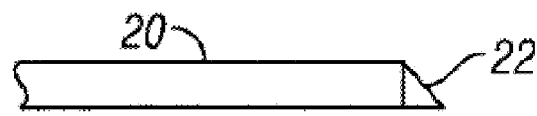
FIG. 2D illustrates a distal portion of the penetrating guidewire according to certain embodiments.
Figure 2E:
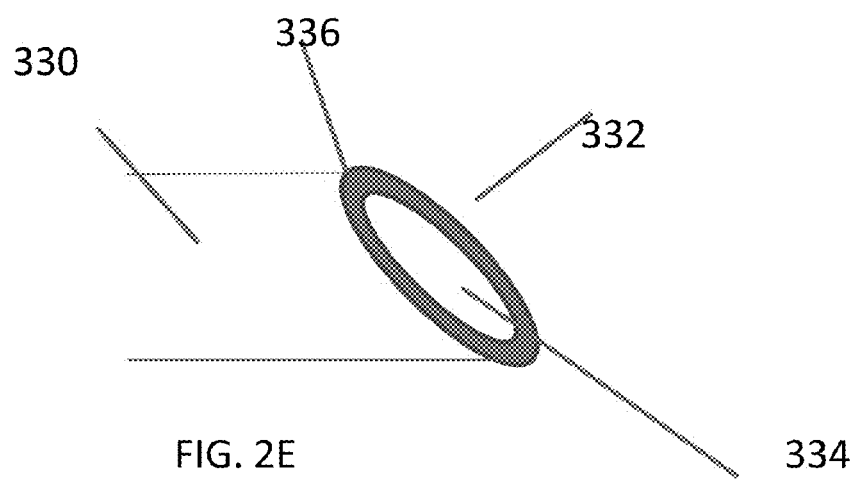
FIG. 2E depicts a needle according to certain embodiments.
Figure 2F:
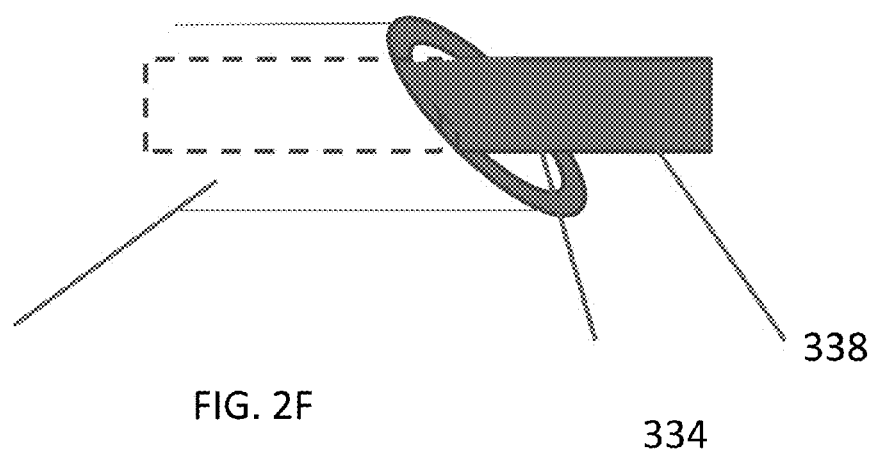
FIG. 2F depicts a needle having a cauterizing member moveably disposed therein according to certain embodiments.

FIGS. 2C-2E illustrate variations of a penetrating guidewire and needle suitable for use with the catheter systems of the invention, A penetrating guidewire 18 is shown in FIGS. 2C and 2D. The penetrating guidewire 18 has a flexible body 20 and a sharp and/or stiff distal tip member 22. The distal tip member 22 allows the guidewire to piece through the vessel walls to create the vascular access opening, FIGS. 2D and 2E illustrate a penetrating needle 330 for use as an alternative to the penetrating guidewire. 18. The penetrating needle 330 is flexible and includes a sharpened distal tip 332 that allows the needle 330 to penetrate through one or more vessel walls to form the vascular access sites. In certain embodiments, the needle 330 defines an opening 334 that leads to a needle lumen. A guidewire (distinct from the penetrating guidewire) or cauterizing member 338 may be extending through the opening 334 of the needle 330. For example, once needle 330 forms openings through a vein and an artery to create the fistula, one can extend a guidewire out of the needle 330 in order to provide guidewire access between the vein and artery. In another example, a cauterizing member 338 (as shown in FIG. 2E) may be extended out of the needle 330 to cauterize/ablate vessel wall tissue surrounding the openings created for the vascular access. The cauterizing member 338 may include one or more ablative elements on its distal end. As an alternative to using a separate cauterizing member 338, the needle 330 may include one or more ablative elements on a distal surface 336 of the needle's distal tip 332. In this manner, the needle 330 itself may form the openings for the fistula as well as treat the vascular access tissue that will eventually form the fistula with the RF/ablative energy. In certain embodiments, the one or more ablative elements of the cauterizing member and/or needle include one or more electrodes.

Using the ablative elements of the needle or the cauterizing member to cauterize/ablate tissue surrounding and forming the fistula (e.g. vascular access site) advantageously inhibits formation of hyperplasia (migration and proliferation of smooth muscle tissue) at the fistula. Hyperplasia of the vascular access site often results in the fistula failing to mature or occludes the vascular access site such that it is effectively an inoperable connection between vein and artery. Thus, the ability to inhibit hyperplasia with the catheter system of the invention increases the maturation potential of the vascular access site.

The proximal end of the needle and/or cauterizing member with the ablative elements can be connected to an energy source that provides energy to the electrodes for ablation. The energy necessary to cauterize the tissue to inhibit hyperplasia can be provided from a number of different sources including radiofrequency, laser, microwave, ultrasound and forms of direct current (high energy, low energy and fulgutronization procedures). Radiofrequency (RF) has become the preferred source of energy for ablation procedures. Any source of energy is suitable for use in the ablation elements of the invention. Preferably, the source of energy chosen does not disrupt the imaging of the vessel during the vascular access creation procedure with the imaging catheter.

In some embodiments, the penetrating guidewire 18 may advance out of the side outlet opening 16, 1106 on a trajectory that forms an angle A of less than 90 degrees relative to the longitudinal axis of the catheter 10 (which is indicated in FIG. 3A), In the particular example shown, this angle A is approximately 65 degrees. The needle 330, 1106 when utilized, may also follow the same trajectory.

According to certain aspects, the catheter system 10 includes an imaging assembly 38 (for example, in FIGS. 2A, 2B, 3A, FIGS. 5, and 6A-6C). The imaging assembly 38 may comprise an on-board imaging apparatus located on or in the catheter 12 that is useable to image the target location for fistula formation (e.g. to which it is desired to advance the penetrating guidewire 18 to form the opening in the first and second vessels). Any suitable type of imaging transducer may be used, including ultrasound, fiber optic (e.g., angioscopic), optical (e.g., optical coherence tomography, etc, (which are described in more detail hereinafter), As shown in FIG. 3A, the imaging assembly 38 is a phased array intravascular ultrasound (IVUS) transducer that images 360 degrees around the catheter 12. According to certain embodiments, the imaging assembly 38 also comprises an annular array of individual crystals or elements coupled to a multiplex circuit. The multiplex circuit is in turn coupled to leads 44, 46 which extend through the catheter 12 and into cable 47. Cable 47 is connectable to an image processing console 31 which houses image processing electronics as well as the monitor 30 in accordance with IVUS technology well known in the art. When activated, the imaging transducer 38 emits ultrasound signals and receives back echoes or reflections which are representative of the nature of the surrounding environment. The imaging transducer 38 provides an imaging signal from which an image of the surrounding structures can be created by signal processing apparatus located in an imaging console 31 and displayed on screen 30. A suitable IVUS phased array transducer as well as the accompanying circuitry and imaging console 31 may be obtained commercially from Volcano Corporation of Rancho Cordova, Calif. or Intravascular Research Limited (United Kingdom).

In preferred embodiments, the imaging assembly 38, in addition to imaging, also provides for characterization of tissue within the vessel. For tissue characterization, the image data obtained with the imaging assembly 38 is processed in a manner that allows one to determine the differences between various tissue and objects within the lumen. For example, tissue characterization allows one to differentiate blood from tissue boundaries, Particular, this tissue/blood differentiation allows one to clearly differentiate assess the tissue and lumens of the first and second vessels that are the targeted subjects of the vascular access site. For characterization of biological and/or foreign materials, a spectral analysis is applied to the image data, which involves examining the energy of the returned acoustic signal (or optical signal) at various frequencies.

Spectral analysis is useful for characterizing and determining the nature of the tissue, blood, and any presence of foreign objects. Blood, for example, generally exhibits a different spectral signal than tissue. As such, spectral analysis can be used to determine the tissue lumen/blood border. In addition, a plaque deposit, for example, will typically have different spectral signatures than nearby vascular tissue without such plaque, allowing discrimination between healthy and diseased tissue. Also a metal surface, such as a stent, will have a different spectral signal. Such signal processing may additionally include statistical processing (e.g., averaging, filtering, or the like) of the returned ultrasound signal in the time domain. Other signal processing techniques known in the art of tissue characterization may also be applied. Suitable types of signal processing for characterization, including spectral analysis, are described in more detail hereinafter.

Tissue and object characterization also allows one to determine the type and nature of a condition at the desired location for the vascular access site (e.g. the first and the second vessel being connected). For example, in addition to identifying a stenosis, thrombosis, or infection at the vascular access site, the tissue characterization can assist in assessing risk of the condition, e.g., the severity of the neointimal hyperplasia, the presence and consistency of any atheroma material (e.g., level of calcification), and the severity of the thrombus.

Optionally, the catheter body 12 of the system 10 may incorporate an orientation indicating element 28 which provides, on a monitor screen 30 an indication of the trajectory on which the penetrating guidewire 18 will advance from the catheter body 12 relative to the location of the intended target to which it is desired to advance the penetrating guidewire 18, As explained in more detail below, this orientation indicating element 28 may comprise an radiopaque marker that may be imaged by an imaging apparatus located either on/in the catheter 12 or elsewhere (e.g., a fluoroscope or other extracorporeal imaging device). In addition to radiopaque markers, the orientation indicating element 28 may be another physical marker or an electrical marker that allows one to determine the relative position of the side exit port 16 within a vessel. For example, the indicator allows one to determine a direction that the penetrating guidewire 18 will subsequently advance out of side outlet opening 16, As a result, this optional orientation indicating element 28 provides information which the operator may use to make any necessary adjustments in the position and rotational orientation of the catheter body 12 in situ ensure (or at least increases the probability) that the penetrating guidewire 18 will subsequently advance to the intended target location and not some other location. One specific example of this orientation element 28 is shown in FIGS. 3A through 4B and described in detail below. Other examples of the various types of orientation elements 28 that may be used include but are not limited to those described in U.S. Pat. No. 5,830,222 (Makower), U.S. Pat. No. 6,068,638 (Makower), U.S. Pat. No. 6,159,225 (Makower), U.S. Pat. No. 6,190,353 (Makower, et al.), U.S. Pat. No. 6,283,951 (Flaherty, et al.), U.S. Pat. No. 6,375,615 (Flaherty, et al.), U.S. Pat. No. 6,508,824 (Flaherty, et al.), U.S. Pat. No. 6,544,230 (Flaherty, et al.), U.S. Pat. No. 6,655,386 (Makower et al.), U.S. Pat. No. 6,579,311 (Makower), U.S. Pat. No. 6,602,241 (Makower, et al.), U.S. Pat. No. 6,655,386 (Makower, et al.), U.S. Pat. No. 6,660,024 (Flaherty, et al.), U.S. Pat. No. 6,685,648 (Flaherty, et al.), U.S. Pat. No. 6,709,444 (Makower), U.S. Pat. No. 6,726,677 (Flaherty, et al.) and U.S. Pat. No. 6,746,464 (Makower) as well as United States Patent Application Publication 2006/0241342 (Macaulay et al.) entitled Optically Guided Penetration Catheters and Their Methods of Use, the entire disclosure of each such patent and published patent applications being expressly incorporated herein by reference.

Figure 4A:
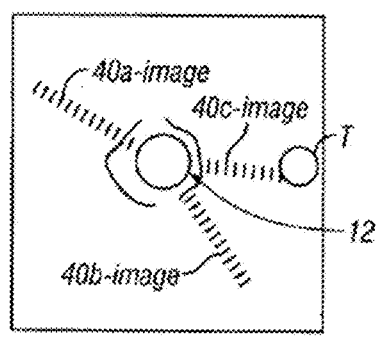
FIG. 4A is a schematic diagram of a monitor display indicating that the catheter of FIG. 1 is in an incorrect rotational orientation relative to the target.
Figure 4B:
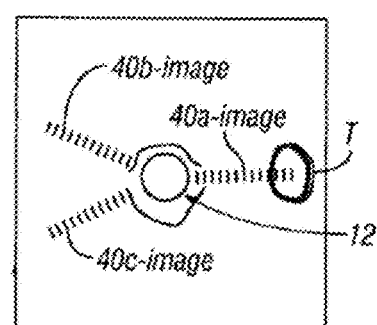
FIG. 4B is a schematic diagram of a monitor display indicating that the catheter of FIG. 1 is in a correct rotational orientation relative to the target.

As shown in FIGS. 2A, 3A-3D, the orientation element 28 may comprise a marker structure 40 that provides a predictive trajectory indication on a displayed image of the target. In this particular example, the orientation element 28 includes a marker structure 40 which includes imagable marker members 40*a*, 40*b* and 40*c* This marker structure 40 is mounted on or in the catheter body 12 in a known circumferential orientation relative to the side outlet port 16 or to the trajectory on which the penetrating guidewire 18 is expected to advance out of the side outlet opening 16. As seen in FIGS. 4A and 4B, the three imagable marker members 40*a*, 40*b* and 40*c* create corresponding images or artifacts (labeled as 40*a*-image, 40*b*-image and 40*c*-image) on the monitor 30 along with an image of the true blood vessel lumen or other target location T. One of these members 40*a* is specifically positioned to provide an image that is visually distinguishable from the others and which corresponds to the expected trajectory of the penetrating guidewire 18 so that the image (40*a*-image) created by that member 40*a* serves as the trajectory indicator. As seen in FIG. 4A, if the catheter body 12 is in an incorrect rotational orientation, the trajectory indicator 40*a*-image does not extend into the target T but rather extends in a direction away from the target T. However, as seen in FIG. 4B, after the catheter body 12 has been rotated to the correct rotational orientation, the trajectory indicator 40*a*-image extends directly toward or into the image of the target T.

It will be appreciated that, as an alternative to the use of a physical marker structure, the imaging assembly 38 could be mounted in a fixed position and a selected one (or selected ones) of the individual imaging elements (e.g., crystals) of the phased array may be selected as being in longitudinal alignment with the side outlet opening 16 or otherwise located so as to be indicative of the trajectory on which the penetrating guidewire 18 will subsequently advance from the catheter body 12. The selected imaging element(s) will thus serve as penetrator-path-indicating imaging element(s) and will be electronically identified so as to form a visual penetrator path indicator (e.g., a line or pointer) on the monitor 30 of the imaging console 31.

Figure 5:
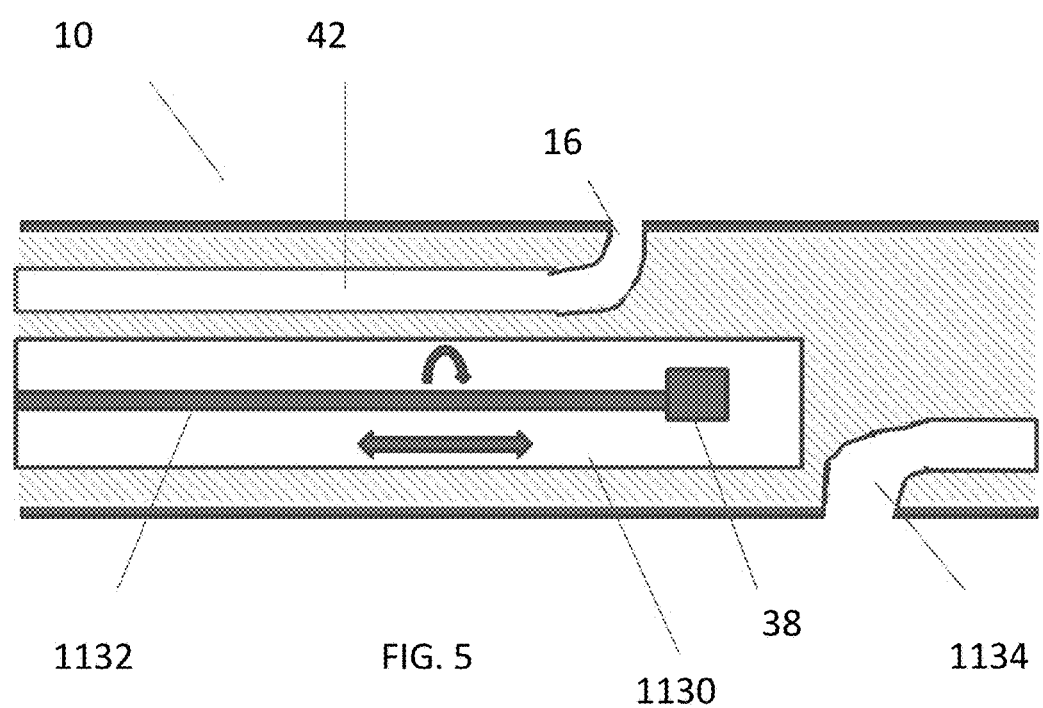
FIG. 5 illustrates a catheter system according to certain embodiments with a rotational imaging assembly.

As shown in FIGS. 2A, 2B, and 3A, the imaging assembly 38 is position within or surrounding the catheter body 12 in a relatively fixed location. In an alternative embodiment, the imaging assembly 38 may include a rotational imaging assembly that rotates and translates longitudinally within an imaging lumen 1130. FIG. 5 depicts a cross-section of a catheter 10 with a rotational imaging assembly 38. The rotational imaging assembly, as shown, is coupled to drive shaft 1132 that allows for the rotation and translation of the rotational imaging assembly 38. As shown, the imaging lumen 1130 is separate from the needle lumen 48. FIG. 5 also depicts an embodiment of the catheter system 10 that includes a rapid-exchange guidewire lumen 1134. The rapid exchange guidewire lumen 1134 is configured to receive a tracking guidewire.

FIGS. 6A-6C illustrate an additional embodiment of the catheter system 10 that allows for imaging in a plane that is in front of the catheter system 10. In this aspect, the imaging assembly 38 is a "forward looking" imaging assembly that image an object a distance in front of the imaging element. As shown in FIGS. 6A and 6B, the imaging assembly 38 is located at the distal portion of the catheter system 10. The imaging assembly 38 at least partially surrounds the distal portion. In preferred embodiments, the forward-looking imaging assembly 38 is an ultrasound transducer array that surrounds at least a portion of the distal end 1140 of the catheter system 10. In the forward-looking embodiment, the exit port 1142 for the penetrating guidewire 18 or needle 330, 1110 is located at the distal end 1140 of the catheter system. As shown in FIGS. 6A and 6B, the needle 1110 (or 330) can be translated longitudinally out of the exit port 1140 to form the openings for vascular access creation. A benefit of the forward looking aspect is that the imaging assembly 38 is able to image tissue in front of the catheter system 10, and is not limited to imaging tissue parallel to the catheter system 10, Like the needle 330 of the catheter system 10, the needle 1110 may include a lumen through which a guidewire or cauterizing member may be extended (See FIG. 2E-2F). In addition, the needle 1110 may similarly include one or more ablation elements.

In certain embodiments, the forward-looking imaging assembly 38 images in a C-mode image plane as illustrated in FIGS. 6B and 6C. The C-mode image plane is perpendicular to the axis of an intraluminal device and spaced in front of the imaging assembly 38. The imaging signals are transmitted at an arbitrary angle from an axis of the imaging element to image a cross-section in front of the imaging element. Alternatively or in addition to, the imaging assembly 38 can image in a B-mode image in a plane that extends in a forward direction from the imaging element and parallel to the axis of the catheter (as shown in FIG. 6C). FIG. 6C exemplifies the beamformer geometry and imaging planes of the imaging assembly 38 when imaging in the forward C-mode and forward B-mode.

Examples of forward-looking ultrasound assemblies are described in U.S. Pat. Nos. 7,736,317, 6,780,157, and 6,457,365, and in Yao Wang, Douglas N. Stephens, and Matthew O'Donnellie, "Optimizing the Beam Pattern of a Forward- Viewing Ring-Annular Ultrasound Array for Intravascular Imaging", Transactions on Ultrasonics, Ferroelectrics, and Frequency Control, vol. 49, no. 12, December 2002. Examples of forward-looking optical coherence tomography assemblies are described in U.S. Publication No. 2010/0220334, Fleming C. P., Wang H., Quart, K. J., and Rollins A. M., "Real-time monitoring of cardiac radio-frequency ablation lesion formation using an optical coherence tomography forward-imaging catheter.," J. Biomed, Opt. 15, (3), 030516-030513 ((2010)), and Wang H, Kang W, Carrigan T, et al; In vivo intracardiac optical coherence tomography imaging through percutaneous access: toward image-guided radio-frequency ablation. J. Biomed. Opt. 0001; 16(11): 110505-110505-3. doi:10.1117/1.3656966. In certain aspects, an imaging assembly 38 includes both side-viewing and forward-looking capabilities. These imaging assemblies utilize different frequencies that permit the imaging assembly to isolate between forward looking imaging signals and side viewing imaging signals. For example, the imaging assembly is designed so that a side imaging port is mainly sensitive to side-viewing frequencies and a forward viewing imaging port is mainly sensitive to forward viewing frequencies. Example of this type of imaging element is described in U.S. Pat. Nos. 7,736,317, 6,780,157, and 6,457,365.

FIGS. 7A-7D illustrate use of a catheter system 10 (as depicted in FIG. 2A) to form a vascular access site. While in reference to the catheter system 10 of FIGS. 2A and 3A, it is understood that the methods shown in FIGS. 7A-7D are applicable to the various embodiments of the catheter system 10 (such as those shown in FIGS. 2B, 5, 6A-6C, for example).

Figure 7A:
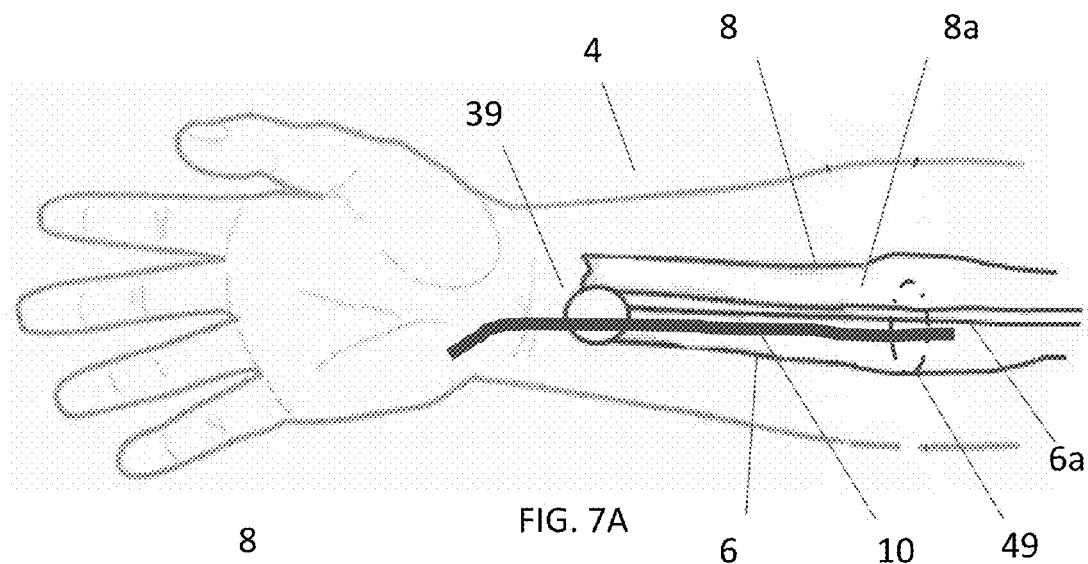
FIG. 7A illustrates imaging with a catheter system according to certain embodiments.

As shown in FIG. 7A, the catheter system 10 is inserted into an insertion site 39 of a limb 4 in order to create a vascular access site for hemodialysis. The catheter system 10 may be introduced over a tracking guidewire (not shown). The catheter system 10 is introduced into a first vessel (as shown artery 6, but may alternatively be vein 8). The catheter system 10 utilizes imaging assembly 38 to image tissue within the vessel 6. The imaging assembly 38 allows for one to obtain cross-sectional image data in order to determine an ideal position for vascular access. The scope of the imaging data is illustrated by imaging beam 49.

According to certain embodiments, the catheter system 10 allows one to visualize and differentiate the first vessel that it is currently disposed in (e.g. artery 6) as well as a second vessel (e.g. vein 8) positioned next to the first vessel. The first and second vessels are utilized to form the fistula. The ability to image both vessels used to form the fistula allows one to ensure that the catheter system 10 is positioned in such a manner that the first vessel is close enough to the second vessel such that a vascular access site can be created between the two vessels 6, 8. That is, visualization of both vessels 6, 8 allows one to precisely determine the ideal location for vascular access and where the needle or penetrating guidewire can be extended such that it creates the vascular access openings in both vessels 6, 8.

Figure 7B:
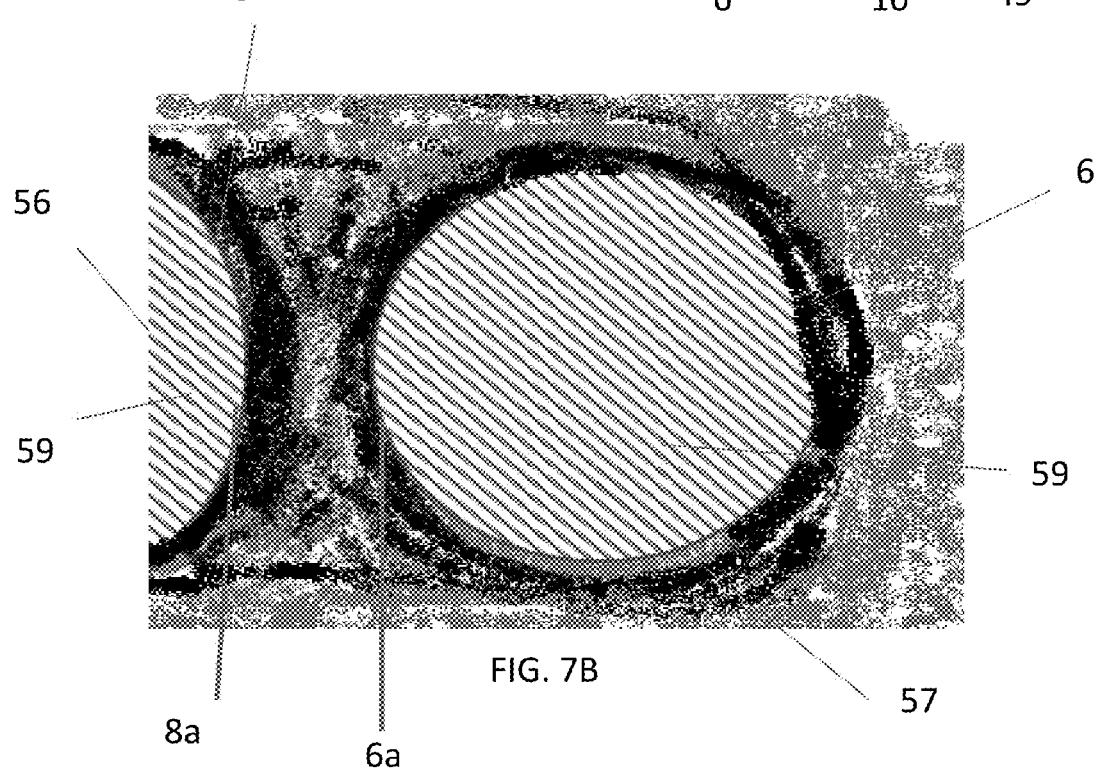
FIG. 7B depicts a tomographical image obtained with a catheter system according to certain embodiments.

FIG. 7B illustrates a tomographical view of image data obtained by the imaging assembly 38. As shown in FIG. 7B, the tomographical image shows first vessel 6 (in which the catheter system is disposed) as well as a portion of second vessel 8 next to the first vessel 6. The lumen 57 and vessel wall 6a of the first vessel 6 as well as the lumen 56 and vessel wall 8a of second vessel 8 can be visualized in the tomographical image. In certain embodiments, the lumens 57, 56 and the vessel walls 6a, 8a can be further differentiated using tissue characterization techniques (e.g. spectral analysis) that highlight differences between blood within the lumen and the vessel tissue. For example, any blood within the lumens 57, 56 provides a different spectral signal than the spectral signal of the vessel walls 6a, 8a. Based on the different spectral signals, processing techniques can be used to apply different colors to the imaged blood and the imaged tissue. For example, the blood within the lumen can be shown in red (as depicted in FIG. 7B, for example, by the striped lines 59), and the tissue walls can be more clearly defined (e.g. with a graphical circle for example).

Figure 7C:
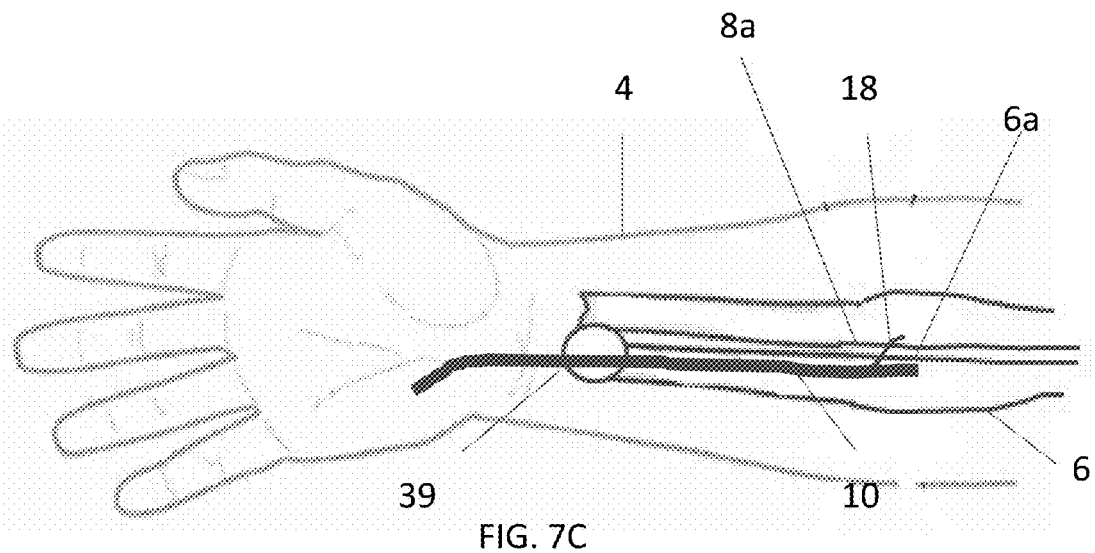
FIG. 7C illustrates formation of openings between a first vessel and a second vessel.
Figure 7D:
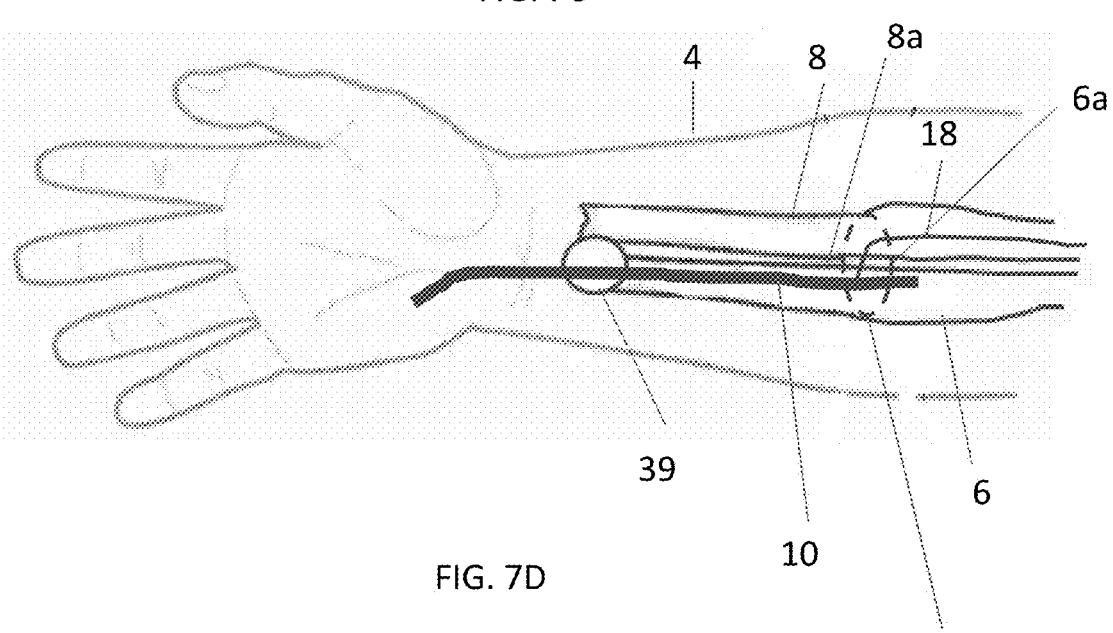
FIG. 7D illustrates imaging the formation of the openings between the first vessel and the second vessel.

Once the target location for the vascular access openings is determined utilizing the imaging assembly 38, the penetrating guidewire 18 can be deployed from the side exit port 16 (not shown in FIG. 7C). The penetrating guidewire 18 deploys through the vessel wall 6a of the first vessel 6 and the vessel wall 8a of the second vessel 8 to form the openings that will eventually form the vascular access site. The act of penetrating the first vessel 6 and the second vessel 8 can be visualized in real-time using the imaging assembly 38, FIG. 7D illustrates using the imaging assembly 38 to image (as illustrated by imaging beam 49) the penetrating guidewire 18 extending from the artery 6, through the artery wall 6a and vein wall 8b, and into the lumen of the vein 8. In embodiments that utilize a needle with one or more ablation elements or a cauterizing member, after the openings for the vascular access site are created, the tissue surrounding the vascular access site can be cauterized or ablated to prevent formation of hyperplasia in the formed vascular access site.

After the openings for the vascular access site are formed within the vessel and artery, an anastomotic dip can be deployed into the opening. The anastomotic clip facilitates formation of the native fistula by ligating the vein 8 and the artery 6 between the formed openings, which allows the fistula to mature. In certain embodiments, an anastomotic clip is driven through the penetrating guidewire lumen 36 (see FIG. 3A) of the catheter system 10 and over the penetrating guidewire 18. The anastomotic clip may be driven by a push rod that fits within the lumen 36. By driving the anastomotic clip over the penetrating guidewire 18, one is able to deliver the clip directly into the vascular access openings created between the artery 6 and vein 8.

FIGS. 8-11 illustrate apparatus and method of delivering an anastomotic clip between the openings created to form a vascular access site. The imaging assembly 38 can be utilized provide real-time imaging of the clip delivery procedure.

Figure 8:
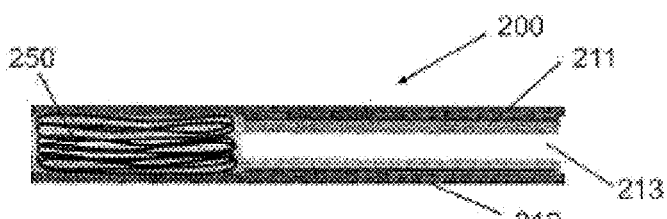
FIGS. 8-11 illustrate introducing an anastomotic clip into the created openings between a first vessel and a second vessel.

FIG. 8 depicts an anastomotic clip deployment apparatus 200 consistent with the present invention that can be used to deploy an anastomotic clip over a guidewire and into the openings created for the vascular access site. Apparatus 200 is a flexible, catheter device, which includes a sliding core, core 211, which has a lumen 213, from its proximal end, not shown, to its distal end, to allow placement over a guidewire, such as penetrating guidewire 18. The apparatus 200 may be driven through the penetrating guidewire lumen 36 of catheter 10, and thus, in certain embodiments, the anastomotic clip deployment apparatus is configured to fit within the penetrating guidewire lumen 26. Alternatively, after a guidewire is placed in the vascular access site via the catheter 10, the catheter 10 may be removed and the apparatus may be introduced separately over the guidewire.

Apparatus 200 includes outer sheath 212, which surrounds and slidingly receives core 211. Located at or near the distal end of apparatus 200, is a preloaded anastomotic clip, clip 250, which is a self-expanding device constrained by outer sheath 212 which can be deployed to secure and create a fistula between an artery and a vein, such as an artery 6 and vein 8 (in FIGS. 7A-7D) or at another location such as the thigh of a patient or other peripheral vascular location. Clip 250 can be deployed by advancing core 211 forward while maintaining outer sheath 212 in a relatively fixed position; by retracting sheath 212 while maintaining core 211 in a relatively fixed position; or by both advancing core 211 and retracting outer sheath 212. A deployment trigger and trigger mechanism, not shown, may be incorporated into apparatus 200 such that the retraction and/or advancement steps are accomplished by activating the trigger, such that timing, relative timing, and advancement and retraction distances are predetermined by the trigger mechanism. In a preferred embodiment, some amount of advancement and retraction are accomplished simultaneously.

Figure 9:
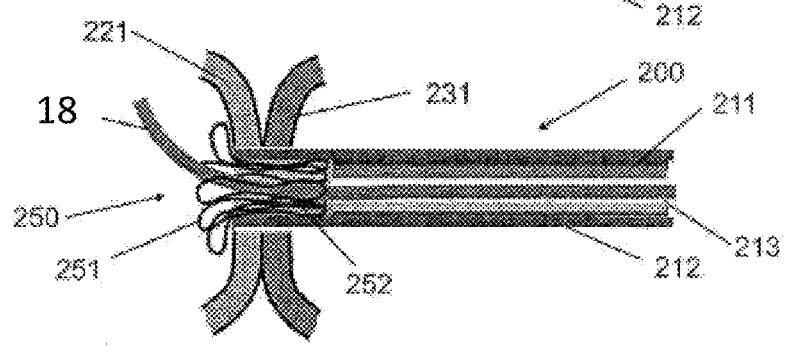

FIG. 9 depicts apparatus 200 deployed over a guidewire 18, such that it passes from a vein and artery in the forearm of a patient. Guidewire 18 is shown passing through arterial wall 231 and venous wall 221, Outer sheath 212 is shown passing through both arterial wall 231 and venous wall 221 to assist in the deployment of clip 250. In order to cross through the vessel walls, apparatus 200 may include a flow path-enlarging element such as an integrated balloon element; and/or apparatus 200 may include a dilating slope on one or more distal ends. Apparatus 200 of FIG. 8 depicts clip 250 being placed from artery to vein, however it should be appreciated that a vein to artery placement can be similarly accomplished by apparatus 200 and would result in a similarly placed clip 250.

In FIG. 9, apparatus 200 is inserted over a guidewire 242, which can be placed similar to guidewire 18 of FIGS. 7A-7D, such as a guidewire placed from a first vessel to a second vessel. In an alternative embodiment, catheter 200 can be inserted without guidewire 18, such as through the use of visualization or other percutaneous techniques. Shown in FIG. 9, dip 250 is partially deployed with distal end 251 of clip 250 expanded and pulled against venous wall 221. Deployment is initiated such as by advancing core 211 while maintaining outer sheath 212 in a fixed position; by retracting sheath 212 while maintaining core 211 in a fixed position; or by both advancing core 211 and retracting sheath 212, preferably in a simultaneous movement. Proximal end 252 of clip 250 remains constrained by outer sheath 212. During the deployment process, apparatus 200 or any portion of apparatus 200 can be retracted while injecting contrast medium. Contrast medium can be injected through apparatus 200, or through a venous catheter or separate arterial catheter. Contact of the distal end 251 of clip 250 can be confirmed by visualizing bulging of either or both the venous wall 221 and the arterial wall 231 during a contrast medium injection.

Figure 10:
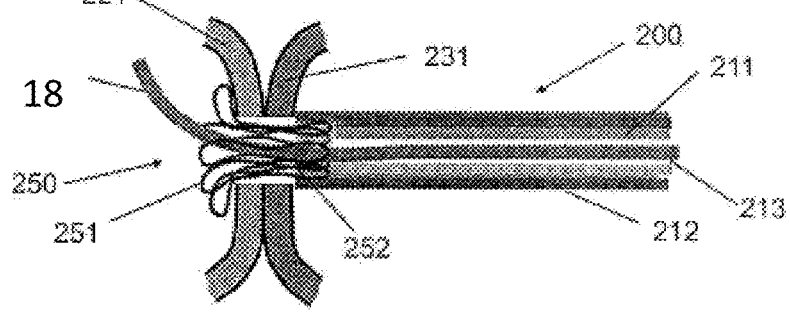

In FIG. 10, clip 250 has been further deployed, and outer sheath 212 retracted to expose venous wall 221 and arterial wall 231. In an alternative embodiment, outer sheath 212 does not pass through arterial wall 231 and/or venous wall 221 and clip 250 is pushed through both walls during deployment.

Figure 11:
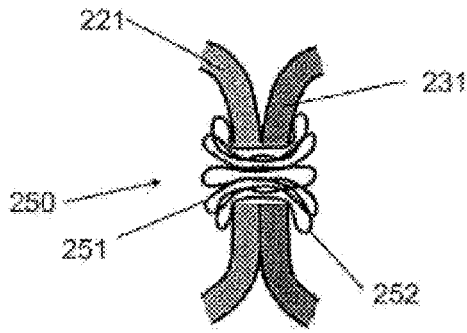

FIG. 11 depicts a fully deployed clip 250, providing an anastomotic connection between arterial wall 231 and venous wall 221 such as to provide a flow path, or fistula, between an artery and vein such as an artery or vein in an arm or leg of the patient, Clip 250 can provide numerous functions as has been described hereinabove including but not limited to: scaffolding an opening between the first vessel and the second vessel; reducing neointimal proliferation into the fistula flow path; preventing tissue from protruding into the fistula flow path; placing a portion of the first vessel wall in tension with the tissue of the second vessel wall; reducing bleeding of the tissue neighboring the fistula; enhancing healing of the tissue neighboring the fistula; and combinations thereof. In FIG. 11, guidewire 18 has been removed and the procedure can be considered complete. In a preferred embodiment, guidewire 18 remains in place, and subsequent operations can be performed to enhance the outcomes and/or therapeutic benefits of the procedure, or to complete one or more other interventional procedures such as those performed in either the starting vessel, or target vessel by way of the starting vessel. For example, a flow measurement procedure may be performed, and flow adjusted such as through further dilation of clip 250. The cross-section of the flow thru lumen of clip 250 may be circular or oval and shape, and the dilating apparatus, such as a dilating balloon, have a similar cross-section. In an alternative, preferred embodiment, clip 250 has additional functionality to improve the long-term patency of the fistula or otherwise provide improved therapy to the patient. Improved functionality of clip 250 may include the integration of an agent, such as an antibacterial, anti-thrombogenic, anti-prolific, or other agent. Clip 250 may also a covering along a part or the entirety of its length, such as a covering consisting of one or more of: polytetrafluoroethylene; Dacron™ material; Nitinol™ alloy; stainless steel; urethane; polyethylene; silicone; carbon and carbon compounds.

For embodiments that utilize a needle 330, 1106, a guidewire (distinct from the penetrating guidewire) can be deployed from the needle 330, 1106 to create guidewire access between the artery and the vein. After the guidewire is placed, the needle 330, 1106 can be retracted or removed such that an anastomotic clip may be delivered between the created openings for fistula formation in the same manner as described in FIGS. 8-11 for the penetrating guidewire.

Catheter systems of the invention include an imaging assembly 38 that provides for guided vascular access creation. The imaging assembly may be and ultrasound imaging assembly, photoacoustic imaging assembly, optical coherence tomography imaging assembly, or combination thereof.

The imaging assembly may be an intravascular ultrasound (IVUS) imaging assembly. The ultrasound probe can either be either a rotating transducer (as in FIG. 5) or an array of circumferentially positioned transducers figures (e.g. FIGS. 2A-2B, 3A, 6A-6C). The proximal end of the catheter is attached to computerized imaging console. The IVUS imaging element (i.e. ultrasound probe) includes transducers that image the tissue with ultrasound energy (e.g., 20-50 MHz range) and image collectors that collect the returned energy (echo) to create an intravascular image. The imaging transducers and imaging collectors are coupled to signal lines that run through the length of the catheter and couple to the computerized ultrasound equipment.

IVUS imaging assemblies produce ultrasound energy and receive echoes from which real time ultrasound images of a thin section of the blood vessel are produced. The imaging transducers of the imaging element are constructed from piezoelectric components that produce sound energy at 20-50 MHz. The image collectors of the imaging element comprise separate piezoelectric elements that receive the ultrasound energy that is reflected from the vasculature. Alternative embodiments of imaging assembly may use the same piezoelectric components to produce and receive the ultrasonic energy, for example, by using pulsed ultrasound. That is, the imaging transducer and the imaging collectors are the same. Another alternative embodiment may incorporate ultrasound absorbing materials and ultrasound lenses to increase signal to noise.

IVUS data is typically gathered in segments where each segment represents an angular portion of an IVUS image. Thus, it takes a plurality of segments (or a set of IVUS data) to image an entire cross-section of a vascular object. Furthermore, multiple sets of IVUS data are typically gathered from multiple locations within a vascular object (e.g., by moving the transducer linearly through the vessel). These multiple sets of data can then be used to create a plurality of two-dimensional (2D) images or one three-dimensional (3D) image.

IVUS imaging assemblies and processing of IVUS data are described in further detail in, for example, Yock, U.S. Pat. Nos. 4,794,931, 5,000,185, and 5,313,949; Sieben et al., U.S. Pat. Nos. 5,243,988, and 5,353,798; Crowley et al., U.S. Pat. No. 4,951,677; Pomeranz, U.S. Pat. No. 5,095,911, Griffith et al., U.S. Pat. No. 4,841,977, Maroney et al., U.S. Pat. No. 5,373,849, Born et al., U.S. Pat. No. 5,176,141, Lancee et al., U.S. Pat. No. 5,240,003, Lancee et al., U.S. Pat. No. 5,375,602, Gardineer et al., U.S. Pat. No. 5,373, 845, Seward et al., Mayo Clinic Proceedings 71(7):629-635 (1996), Packer et al., Cardiostim Conference 833 (1994), "Ultrasound Cardioscopy," Eur. J.C.P.E. 4(2):193 (June 1994), Eberle et al., U.S. Pat. No. 5,453,575, Eberle et al., U.S. Pat. No. 5,368,037, Eberle et al., U.S. Pat. No. 5,183, 048, Eberle et al., U.S. Pat. No. 5,167,233, Eberle et at., U.S. Pat. No. 4,917,097, Eberle et at., U.S. Pat. No. 5,135,486, U.S. Pub. 2009/0284332; U.S. Pub. 2009/0195514 A1; U.S. Pub. 2007/0232933; and U.S. Pub. 2005/0249391 and other references well known in the art relating to intraluminal ultrasound devices and modalities.

OCT is a medical imaging methodology using a miniaturized near infrared light-emitting probe. As an optical signal acquisition and processing method, it captures micrometer-resolution, three-dimensional images from within optical scattering media (e.g., biological tissue). Recently it has also begun to be used in interventional cardiology to help diagnose coronary artery disease. OCT allows the application of interferometric technology to see from inside, for example, blood vessels, visualizing the endothelium (inner wall) of blood vessels in living individuals.

OCT systems and methods are generally described in Castella et al., U.S. Pat. No. 8,108,030, Milner et al., U.S. Patent Application Publication No. 2011/0152771, Condit et al., U.S. Patent Application Publication No. 2010/0220334, Castella et al., U.S. Patent Application Publication No. 2009/0043191. Milner et al., U.S. Patent Application Publication No. 2008/0291463, and Kemp, N., U.S. Patent Application Publication No. 2008/0180683, the content of each of which is incorporated by reference in its entirety.

In OCT, a light source delivers a beam of light to an imaging device to image target tissue. Light sources can include pulsating light sources or lasers, continuous wave light sources or lasers, tunable lasers, broadband light source, or multiple tunable laser. Within the light source is an optical amplifier and a tunable filter that allows a user to select a wavelength of light to be amplified. Wavelengths commonly used in medical applications include near-infrared light, for example between about 800 nm and about 1700 nm.

Aspects of the invention may obtain imaging data from an OCT system, including OCT systems that operate in either the time domain or frequency (high definition) domain. Basic differences between time-domain OCT and frequency-domain OCT is that in time-domain OCT, the scanning mechanism is a movable mirror, which is scanned as a function of time during the image acquisition. However, in the frequency-domain OCT, there are no moving parts and the image is scanned as a function of frequency or wavelength.

In time-domain OCT systems an interference spectrum is obtained by moving the scanning mechanism, such as a reference mirror, longitudinally to change the reference path and match multiple optical paths due to reflections within the sample. The signal giving the reflectivity is sampled over time, and light traveling at a specific distance creates interference in the detector. Moving the scanning mechanism laterally (or rotationally) across the sample produces two-dimensional and three-dimensional images. In frequency domain OCT, a light source capable of emitting a range of optical frequencies excites an interferometer, the interferometer combines the light returned from a sample with a reference beam of light from the same source, and the intensity of the combined light is recorded as a function of optical frequency to form an interference spectrum. A Fourier transform of the interference spectrum provides the reflectance distribution along the depth within the sample.

Several methods of frequency domain OCT are described in the literature. In spectral-domain OCT (SD-OCT), also sometimes called "Spectral Radar" (Optics letters, Vol. 21, No. 14 (1996) 1087-1089), a grating or prism or other means is used to disperse the output of the interferometer into its optical frequency components. The intensities of these separated components are measured using an array of optical detectors, each detector receiving an optical frequency or a fractional range of optical frequencies. The set of measurements from these optical detectors forms an interference spectrum (Smith, L. M. and C. C. Dobson, Applied Optics 28: 3339-3342), wherein the distance to a scatterer is determined by the wavelength dependent fringe spacing within the power spectrum. SD-OCT has enabled the determination of distance and scattering intensity of multiple scatters lying along the illumination axis by analyzing a single the exposure of an array of optical detectors so that no scanning in depth is necessary. Typically the light source emits a broad range of optical frequencies simultaneously.

Alternatively, in swept-source OCT, the interference spectrum is recorded by using a source with adjustable optical frequency, with the optical frequency of the source swept through a range of optical frequencies, and recording the interfered light intensity as a function of time during the sweep. An example of swept-source OCT is described in U.S. Pat. No. 5,321,501.

Generally, time domain systems and frequency domain systems can further vary in type based upon the optical layout of the systems: common beam path systems and differential beam path systems. A common beam path system sends all produced light through a single optical fiber to generate a reference signal and a sample signal whereas a differential beam path system splits the produced light such that a portion of the light is directed to the sample and the other portion is directed to a reference surface. Common beam path systems are described in U.S. Pat. No. 7,999,938; U.S. Pat. No. 7,995,210; and U.S. Pat. No. 7,787,127 and differential beam path systems are described in U.S. Pat. No. 7,783,337; U.S. Pat. No. 6,134,003; and U.S. Pat. No. 6,421,164, the contents of each of which are incorporated by reference herein in its entirety.

In advanced embodiments, the systems of the invention incorporate focused acoustic computed tomography (FACT), which is described in WO2014/109879, incorporated herein by reference in its entirety.

In yet another embodiment, the imaging assembly for use in methods of the invention is an optical-acoustic imaging assembly. Optical-acoustic imaging apparatus include at least one imaging element to send and receive imaging signals. In one embodiment, the imaging element includes at least one acoustic-to-optical transducer. In certain embodiments, the acoustic-to-optical transducer is a Fiber Bragg Grating within an optical fiber. In addition, the imaging elements may include the optical fiber with one or more Fiber Bragg Gratings (acoustic-to-optical transducer) and one or more other transducers. The at least one other transducer may be used to generate the acoustic energy for imaging. Acoustic generating transducers can be electric-to-acoustic transducers or optical-to-acoustic transducers.

Fiber Bragg Gratings for imaging provides a means for measuring the interference between two paths taken by an optical beam. A partially-reflecting Fiber Bragg Grating is used to split the incident beam of light into two parts, in which one part of the beam travels along a path that is kept constant (constant path) and another part travels a path for detecting a change (change path). The paths are then combined to detect any interferences in the beam. If the paths are identical, then the two paths combine to form the original beam. If the paths are different, then the two parts will add or subtract from each other and form an interference. The Fiber Bragg Grating elements are thus able to sense a change wavelength between the constant path and the change path based on received ultrasound or acoustic energy. The detected optical signal interferences can be used to generate an image using any conventional means.

Exemplary optical-acoustic imaging assemblies are disclosed in more detail in U.S. Pat. Nos. 6,659,957 and 7,527,594, 7,245,789, 7,447,388, 7,660,492, 8,059,923 and in U.S. Patent Publication Nos. 2008/0119739, 2010/0087732 and 2012/0108943.

In certain embodiments, angiogram image data is obtained simultaneously with the image data obtained from the imaging catheters. In such embodiments, the imaging catheter may include one or more radiopaque labels that allow for co-locating image data with certain positions on a vasculature map generated by an angiogram. Co-locating intraluminal image data and angiogram image data is known in the art, and described in U.S. Publication Nos. 2012/0230565, 2011/0319752, and 2013/0030295.

In certain embodiments, the penetrating guidewire 18 is also a pressure/flow guidewire. In such embodiment, the penetrating guidewire 18 is able to obtain functional flow data within the vessels to assist in determining an ideal location to form vascular access and to assess the vascular access site after formation of the openings and/or after introduction of an anastomotic clip. In such embodiments, the penetrating guidewire may include a pressure sensor, a flow sensor, and combinations thereof. The pressure sensor and the flow sensor may be fiber optic based. Pressure sensors can be used to measure pressure within the lumen and flow sensors can be used to measure the velocity of blood flow. A guidewire with both a pressure sensor and a flow sensor provides information and data for calculating fractional flow reserve (FFR) using pressure readings, and coronary flow reserve (CFR), or similar, using flow readings.

The ability to measure and compare both the pressure and velocity flow to determine an index of resistance of flow within the vessel allows one to determine an ideal placement for vascular access. It has been shown that distal pressure and velocity measurements, particularly regarding the pressure drop-velocity relationship such as Fractional Flow reserve (FFR), Coronary flow reserve (CFR) and combined P-V curves, reveal information about the health of the vessel and its ability to withstand hemodialysis.

A pressure sensor allows one to obtain pressure measurements within a body lumen. A particular benefit of pressure sensors is that pressure sensors allow one to measure of FFR in vessel. FFR is a comparison of the pressure within a vessel at a proximal position and a distal position. The FFR value allows one to assess pressure before and after vascular access creation to determine the impact of the procedure. A pressure sensor can be mounted on the distal portion of penetrating guidewire. The pressure sensor can be formed of a crystal semiconductor material having a recess therein and forming a diaphragm bordered by a rim. A reinforcing member is bonded to the crystal and reinforces the rim of the crystal and has a cavity therein underlying the diaphragm and exposed to the diaphragm. A resistor having opposite ends is carried by the crystal and has a portion thereof overlying a portion of the diaphragm. Electrical conductor wires can be connected to opposite ends of the resistor and extend within the flexible elongate member to the proximal portion of the flexible elongate member. Additional details of suitable pressure sensors that may be used with devices of the invention are described in U.S. Pat. No. 6,106,476. U.S. Pat. No. 6,106,476 also describes suitable methods for mounting the pressure sensor 104 within a sensor housing.

In certain aspects, the penetrating guidewire 18 of the invention includes a flow sensor. The flow sensor can be used to measure blood flow velocity within the vessel, which can be used to assess coronary flow reserve (CFR), or similar. The flow sensor can be, for example, an ultrasound transducer, a Doppler flow sensor or any other suitable flow sensor, disposed at or in close proximity to the distal tip of the guidewire. The ultrasound transducer may be any suitable transducer, and may be mounted in the distal end using any conventional method, including the manner described in U.S. Pat. Nos. 5,125,137, 6,551,250 and 5,873,835.

In certain embodiments, catheter systems of the invention modify flow and pressure guidewires sold under the name FLOWIRE by Volcano Corporation, the pressure guidewire sold under the name PRIMEWIRE PRESTIGE by Volcano Corporation, or both. Those guidewires can be modified to incorporate a tissue penetrating tip.

According to certain aspects of the invention, the obtained image data from the imaging assembly 38 of the catheter system 10 and/or functional flow data is processed to characterize biological material and/or foreign material within the vessels for the vascular access site. The characterization allows one to determine with specificity an ideal location to form a vascular access site. The processing step may be performed by an image processing computer coupled to an imaging catheter (e.g. coupled to the image processing console 31 as in FIG. 2A). The imaging catheter may be directed coupled to the image processing computer or coupled to a system controller that allows for manipulation of the imaging catheter (e.g. coupled by the imaging connector 1112 of FIG. 2B).

Figure 12:
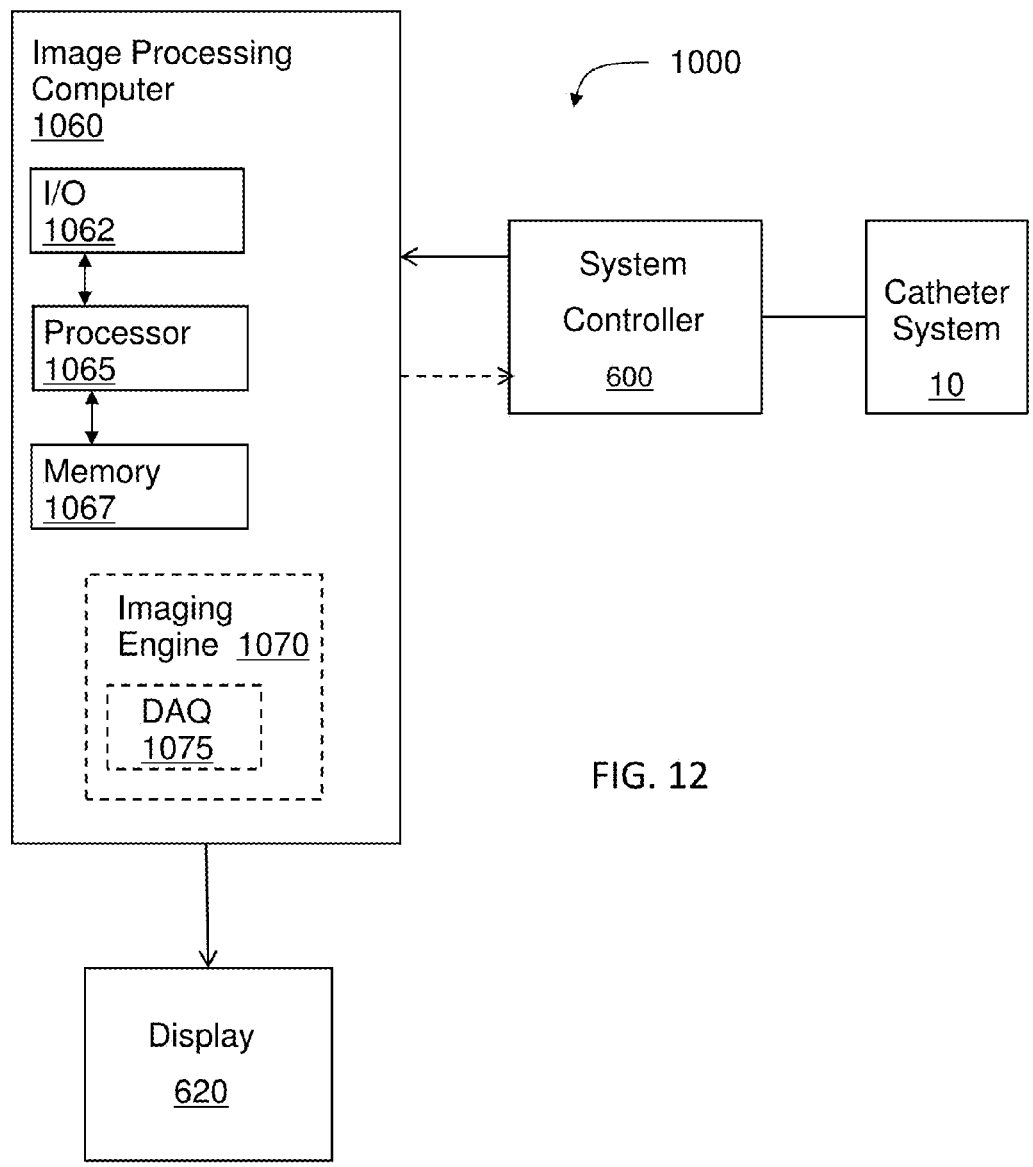
FIG. 12 depicts an image processing system for use with an imaging catheter.

Referring now to FIG. 12, the catheter system 10 may be coupled to and coordinated by a system controller 600. The system controller 600 may control the timing, duration, and amount of imaging. As shown in FIG. 12, the system controller 600 is additionally interfaced with image processing computer 1060. According to certain embodiments, the processor 1065 of the image processing computer 1060 performs tissue/blood characterization, thereby allowing the viewed and assessed images to be the basis for defining parameters for identifying an ideal vascular access creation site. The system 1000 also includes a display 620 and a user interface that allow a user, e.g. a surgeon, to interact with the images (including tissue characterization) and to control the parameters of the treatment.

As shown in FIG. 12, the system controller 600 is interfaced to an image processing computer 1060 that is capable of synthesizing the images and tissue measurements into easy-to-understand images. The image processing computer is also configured to analyze the spectrum of the collected data to determine tissue characteristics, a.k.a. virtual histology. As discussed in greater detail below, the image processing will deconvolve the reflected acoustic waves or interfered infrared waves to produce distance and/or tissue measurements, and those distance and tissue measurements can be used to produce an image, for example an IVUS image or an OCT image. Flow detection and tissue characterization algorithms, including motion-detection algorithms (such as CHROMAFLO (IVUS fluid flow display software; Volcano Corporation), Q-Flow, B-Flow, Delta-Phase, Doppler, Power Doppler, etc.), temporal algorithms, harmonic signal processing, can be used to differentiate blood speckle from other structural tissue, and therefore enhance images where ultrasound energy back scattered from blood causes image artifacts.

In certain embodiments, the image processing may additionally include spectral analysis, i.e., examining the energy of the returned acoustic signal at various frequencies. Spectral analysis is useful for determining the nature of the tissue and the presence of foreign objects. A plaque deposit or neointimal hyperplasia, for example, will typically have different spectral signatures than nearby vascular tissue without such plaque or neointimal hyperplasia, allowing discrimination between healthy and diseased tissue. Also a metal surface, such as a AV graft, will have a different spectral signal. Such signal processing may additionally include statistical processing (e.g., averaging, filtering, or the like) of the returned ultrasound signal in the time domain. The spectral analysis can also be used to determine the tissue lumen/blood border. Other signal processing techniques known in the art of tissue characterization may also be applied. By distinguishing the between the above referenced features within the vessel, one is able to determine the ideal location for creating the vascular access site.

Other image processing may facilitate use of the images or identification of features of interest. For example, the border of a lumen may be highlighted or thrombus or plaque deposits may be displayed in a visually different manner (e.g., by assigning thrombus a discernible color) than other portions of the image. Other image enhancement techniques known in the art of imaging may also be applied. In a further example, similar techniques can be used to discriminate between vulnerable plaque and other plaque, or to enhance the displayed image by providing visual indicators to assist the user in discriminating between vulnerable and other plaque, Other measurements, such as flow rates or pressure may be displayed using color mapping or by displaying numerical values. In some embodiments, the open cross-sectional area of the lumen is colorized with red to represent the blood flux. Thus, by using virtual histology (spectral analysis), methods of the invention allow one to assess the health of the tissue within the vessel such that an ideal location for a vascular access site can be chosen.

In addition to the above disclosed systems, the following systems for detecting and characterizing plaque and biological tissue using virtual histology are disclosed in U.S. Pat. No. 6,200,268 entitled "VASCULAR PLAQUE CHARACTERIZATION" issued Mar. 13, 2001, U.S. Pat. No. 6,381, 350 entitled "INTRAVASCULAR ULTRASONIC ANALYSIS USING ACTIVE CONTOUR METHOD AND SYSTEM" issued Apr. 30, 2002, U.S. Pat. No. 7,074,188 entitled "SYSTEM AND METHOD OF CHARACTERIZING VASCULAR TISSUE" issued Jul. 11, 2006, U.S. Pat. No. 7,175,597 entitled "NON-INVASIVE TISSUE CHARACTERIZATION SYSTEM AND METHOD" issued Feb. 13, 2007, U.S. Pat. No. 7,215,802 entitled "SYSTEM AND METHOD FOR VASCULAR BORDER DETECTION" issued May 8, 2007, U.S. Pat. No. 7,359,554 entitled "SYSTEM AND METHOD FOR IDENTIFYING A VASCULAR BORDER" issued Apr. 15, 2008, and U.S. Pat. No. 7,463, 759 entitled "SYSTEM AND METHOD FOR VASCULAR BORDER DETECTION" issued Dec. 9, 2008.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A method for creating a vascular access site, the method comprising:
  providing a catheter comprising:
    an elongate body comprising a distal end,
    an exit port near the distal end of the elongate body, and
    an imaging assembly operably associated with the elongate body;
  introducing the catheter into a first vessel to generate image data;
  imaging, with the imaging assembly, the first vessel and a second vessel other than the first vessel;
  determining a location to form a vascular access site between the first vessel and the second vessel based on the imaging step;
  extending a penetrating member from inside the catheter out of the exit port of the catheter toward the determined location of the vascular access site such that the penetrating member passes through walls of the first vessel and the second vessel, thereby creating the vascular access site, wherein the penetrating member comprises an interior lumen terminating at a distal tip of a needle; and
  while the penetrating member remains extended out of the exit port to the vascular access site, extending a cauterizing element through the interior lumen of the needle into the vascular access site.

2. The method of claim 1, further comprising the step of extending a guidewire out of the opening of the penetrating member and into the second vessel.

3. The method of claim 2, further comprising the step of delivering, over the guidewire, an anastomotic implant into a fistula.

4. The method of claim 1, wherein the imaging assembly comprises an ultrasound assembly or an optical assembly.

5. The method of claim 1, further comprising the step of processing the image data to identify biological material of the first and second vessels, and wherein the processing comprises determining a blood-tissue border of lumens of the first and second vessels.

6. The method of claim 5, further comprising displaying a cross-sectional image of the lumens of the first and second vessels and the determined blood-tissue border of the lumens of the first and second vessels.

7. The method of claim 6, further comprising colorizing the image to show the blood-tissue borders of the lumens.

8. The method of claim 1 wherein the exit port is located on the distal end of the elongate body so that the penetrating member and the cauterizing element extend out the distal end of the catheter toward the vascular access site.

9. The method of claim 1 wherein the exit port is located on a side of the elongate body so that the penetrating member and the cauterizing element extend out the side of the catheter toward the vascular access site.

* * * * *